United States Patent
Boyle et al.

(10) Patent No.: US 7,030,380 B2
(45) Date of Patent: Apr. 18, 2006

(54) APPARATUS FOR ON-LINE MONITORING QUALITY/CONDITION OF FLUIDS

(75) Inventors: Frederick P. Boyle, Kirtland, OH (US); William P. Taylor, Mentor, OH (US); Michelle M. Graf, Mentor, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 11/255,352

(22) Filed: Oct. 21, 2005

(65) Prior Publication Data

US 2006/0038130 A1    Feb. 23, 2006

Related U.S. Application Data

(63) Continuation of application No. 11/092,077, filed on Mar. 29, 2005, now abandoned, which is a continuation of application No. 10/337,594, filed on Jan. 7, 2003, now abandoned.

(51) Int. Cl.
  *G01N 21/35* (2006.01)
  *G01J 5/02* (2006.01)

(52) U.S. Cl. .............................. 250/339.11; 250/339.12

(58) Field of Classification Search ........... 250/339.11, 250/339.12, 341.1, 341.8; 356/128, 135, 356/136, 237, 244, 300, 326, 346, 451
See application file for complete search history.

(56) References Cited

U.S. PATENT DOCUMENTS

| | | | |
|---|---|---|---|
| 4,835,389 A | 5/1989 | Doyle | 250/343 |
| 5,051,551 A | 9/1991 | Doyle | 250/341 |
| 5,210,418 A | 5/1993 | Harrick et al. | 250/339 |
| 5,506,416 A * | 4/1996 | Rizvi | 250/339.06 |
| 5,818,046 A * | 10/1998 | Rizvi | 250/339.12 |
| 5,875,783 A | 3/1999 | Kullik | 128/204.18 |
| 5,965,899 A | 10/1999 | Little, Jr. | 257/17 |

FOREIGN PATENT DOCUMENTS

| | | |
|---|---|---|
| DE | 19714664 A1 | 10/1998 |
| WO | WO03/030621 A2 | 4/2003 |

OTHER PUBLICATIONS

Corresponding PCT International Publication No. WO 2004/063727A1 published Jun. 29, 2004 and Search Report mailed.

* cited by examiner

*Primary Examiner*—Otilia Gabor
(74) *Attorney, Agent, or Firm*—Teresan W. Gilbert; Michael F. Esposito

(57) ABSTRACT

An apparatus for on-line optical monitoring of the quality and/or chemical condition of a fluid; in particular, a hydrocarbon-based fluid used in transportation and industrial applications. The apparatus includes an IR-transparent internal-reflectance-element (IRE) that has at least one essentially flat surface and at least one convex surface, and at least two IR light paths of uniquely determined central-frequency and bandwidth with light from a source entering a flat surface of the IRE, internally reflecting at least once from at least one convex surface of the IRE that can contact a fluid, exiting a flat surface of the IRE, and being received at a detector. The apparatus also includes electronics to power the source and receive output from the detector of each light path. The apparatus can be controlled to independently monitor the IR light reflected within the IRE at the uniquely determined frequency of each path, and to communicate information relevant to the IR light detected.

18 Claims, 8 Drawing Sheets

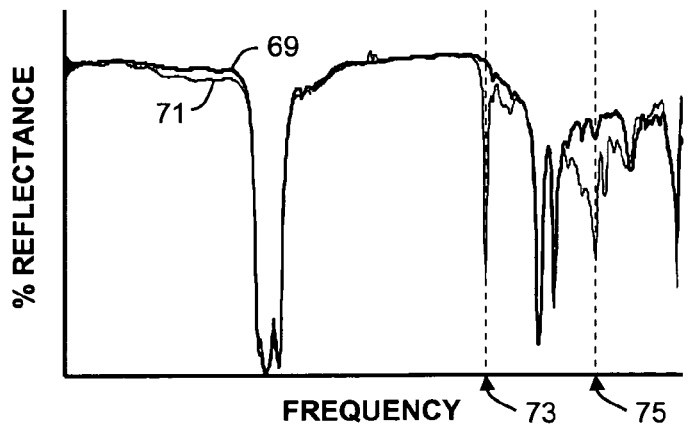
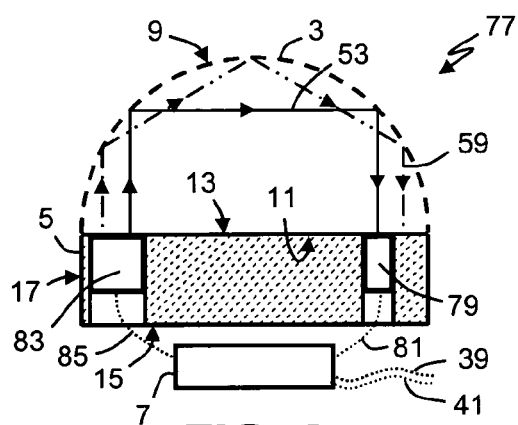
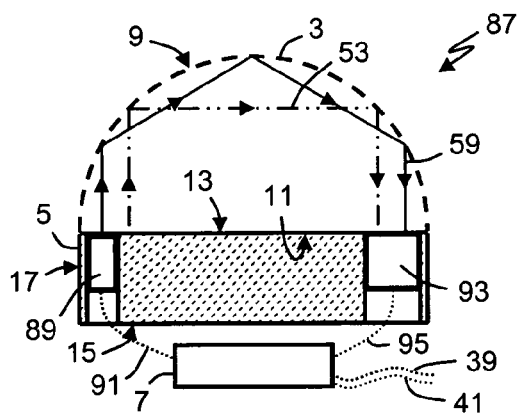
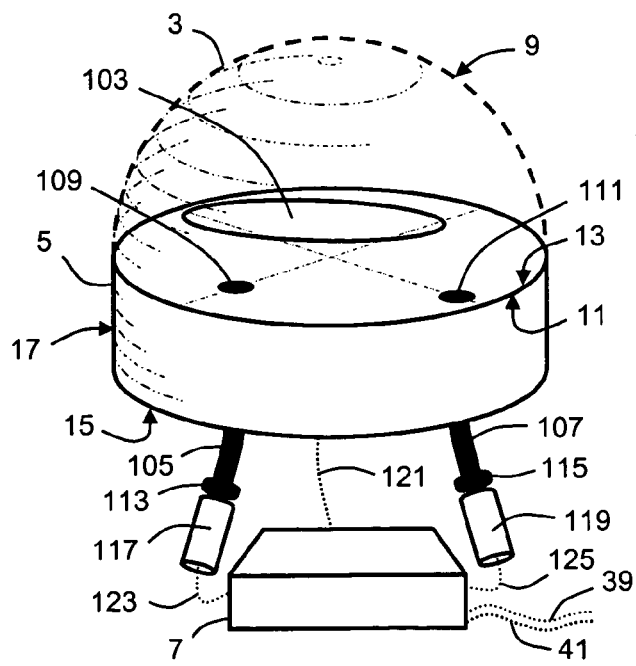

APPARATUS FOR ON-LINE MONITORING QUALITY/CONDITION OF FLUIDS

This application is a continuation of U.S. Ser. No. 11/092,077 filed Mar. 29, 2005 now abandoned, which is a continuation of now abandoned U.S. Ser. No. 10/337,594 filed Jan. 7, 2003 and claims the benefit of said prior applications.

BACKGROUND OF THE INVENTION

The present invention relates to fluid monitoring and fluid analysis. As used herein, a fluid can be either a liquid or a gas. The invention optically monitors fluids on-line (i.e., while in use) such as, e.g., lubricants, natural and/or synthetic motor oils, standard additives and/or adjuncts, combustion engine fuels, other hydrocarbon-based fluids used in transportation and industrial applications. The present invention further relates to an apparatus for on-line analysis of a fluid's quality and/or condition using a fluid's optical absorption to determine, e.g. base fluid, amount or depletion of a performance additives, contamination with unwanted liquids or solids, general degradation of the fluid due to chemical breakdown, or other variables associated with a fluid's type, condition or quality.

Fluids are a critical component for proper operation of many devices and/or processes. For example, lubricants are needed for an internal combustion engine to efficiently provide power over long service life; high quality fuel is needed for proper engine operation with minimal emissions; and metal working fluid is needed for rapid waste metal removal and maximum tool life. Optimum performance is achieved when the fluid in question is of a proper quality for the application. For a particular application, a fluid preferably includes an appropriate base fluid and proper performance additives, e.g., corrosion inhibitors, friction modifiers, dispersants, surfactants, detergents, and the like. During use or consumption, a fluid's condition should remain within determined limits, i.e., chemical and/or other fluid changes should be within proper performance specifications.

Often, device owners and/or process operators depend on suppliers to provide proper quality fluids, and depend on regular level checks and fluid replacement to maintain proper fluid condition. However, the foregoing is inherently limited and does not provide protection against accidental fluid substitution, or catastrophic fluid failure. In addition, regularly timed maintenance intervals can be wasteful if a fluid, with remaining useful life, is prematurely replaced or refreshed. Such premature maintenance, however, is often desirable rather than risk damage or inefficient operation due to overly degraded fluids. In any event, owners and/or operators can minimize fluid maintenance costs without risking damage or inefficient operation if fluid maintenance occurs only at or near the end (natural or otherwise) of fluid's usefulness. Hence, an on-line fluid monitoring method and apparatus is desirable to provide substantially "real-time" determination of a fluid's initial quality and of a fluid's continuing condition during use.

Infrared (IR) spectroscopy is a tool that has long been used to obtain information about a fluid's quality and condition. IR spectroscopy apparatus, typically, either transmits broad-frequency IR light through a fluid of interest, or reflects broad-frequency IR light from a surface of an IR-transparent element of sufficiently high index-of-refraction (known in the art as an internal-reflectance-element or IRE) in contact with the fluid of interest. If no fluid is present in the apparatus, all light frequencies (wavelengths) are equally transmitted or reflected. When a fluid is present, however, IR light is absorbed at specific frequencies associated with particular fluid chemical groups. The amount of IR light absorbed is a function of the particular chemical concentration. Some fluid chemical groups also absorb IR light over a wide frequency range, for example soot in a heavy-duty diesel engine lubricant. Concentration of these groups is determined by comparing shift in IR absorbance at one or more frequencies where absorption due to other groups should not occur; i.e. the shift in baseline absorption is determined. Hence, by analyzing IR spectra for valleys and change baseline absorption, information of fluid quality and condition can be determined.

Despite proven analytical capabilities, IR spectroscopy has remained primarily a laboratory tool. In particular, on-line use of IR spectroscopy for real-time fluid analysis has been essentially limited to monitoring chemical processes in stationary plants due to IR apparatus cost, size, shock and vibration sensitivity, and complexity of data analysis issues. Most of these issues are directly related to monitoring the entire IR spectrum for optimum fluid analysis, which requires the IR apparatus to have relatively large and expensive movable components that are sensitive to shock and vibration, and also requires the apparatus to include relatively expensive data analysis hardware and software.

There are, however, on-line applications where adequate fluid analysis can be obtained by monitoring only a number of discrete frequencies instead of the entire IR spectrum. As used herein, a monitored frequency is a range of frequencies that has a defined central-frequency and bandwidth; hence, all light paths that are described herein for use in monitoring a frequency includes sources, detectors or filters that emit, detect or filter a range of frequencies that has a defined central-frequency and bandwidth. Typically, the number of discrete frequencies needed to adequately analyze a fluid is less than 20, and more typically less than 5; however, applications can require greater than 20 frequencies for adequate analysis. These discrete-frequency applications minimize required data analysis hardware and software, and several approaches have been taken to address the other issues of on-line IR fluid analysis described above.

One discrete-frequency approach uses a fixed prism and discrete detectors at fixed location relative to the prism to monitor the desired frequencies. While this approach minimizes shock and vibration sensitivity issues, apparatus size remains relatively large due to the optical path length needed to get sufficient frequency resolution, that is, to minimize the bandwidth of the frequencies received by the detector. If the apparatus is required by the application to operate over a wide temperature range, operational stability can be an issue due to thermal expansion affecting the optical path through the prism. Also while this approach has reduced apparatus cost, the precision needed to manufacture the prism and placing the detectors still has significant cost.

Another discrete-frequency approach uses a filter, a source or a detector of a desired IR frequency to create a light path, which can include an IR transparent IRE in contact with a fluid, that is cost effective, compact, robust, and minimally affected by temperature fluctuations. Current designs, however, have not effectively solved the problems of how to monitor more than one IR frequency in a single sensor package, especially when a different number of internal reflections is need for each frequency to properly resolve changes in a monitored fluid.

The present invention overcomes limitations of previous approaches to discrete frequency IR apparatus. The present invention is a compact, low-cost, and robust IR apparatus with an IRE that can monitor a multitude of IR frequencies, each having a determined number of reflections in the IRE, over a wide temperature range. The apparatus can be used on-line to provide information relevant to the real-time quality and/or condition of a fluid.

SUMMARY OF THE INVENTION

The present invention is an apparatus for use in determining one or more properties or conditions of a fluid that comprises:
- a) an IR transparent internal reflectance element (IRE) with at least one essentially flat surface and at least one convex surface that can contact a fluid,
- b) at least two IR light paths of uniquely determined frequency with emitted light from a source entering a flat surface of the IRE, internally reflecting at least once from a convex surface of the IRE that can contact a fluid, exiting a flat surface of the IRE, and being received at a detector, and
- c) electronics to: i) power the light paths, ii) independently monitor the amount of light received for each light path, and iii) communicate information relevant to the monitored light reception.

One feature of the invention is that a light path source includes at least one IR light emitter.

Another feature of the invention is that a light path detector includes at least one IR light sensor.

Another feature of the invention is that the unique frequency of a light path is determined by at least one of the following: a) the light path's source only emits light at the determined frequency, b) the light path's detector only receives light at the determined frequency, c) an optical filter of the determined frequency are placed between the light path's source and detector, or d) combinations thereof.

Another feature of the invention is that the amount of light received for a light path can be independently monitored by having a controllable IR source that provides essentially all the path's IR light where at least one of the following occurs: a) the source only emits light at the determined frequency, b) an optical filter of the determined frequency is placed between the source and the IRE, or c) combinations thereof.

Another feature of the invention is that the amount of light received for a light path can be independently monitored by having a controllable IR detector that receives essentially all the path's IR light where at least one of the following occurs; a) the detector only receives light of the determined frequency, b) an optical filter of the determined frequency is placed between the detector and the IRE, or c) combinations thereof.

Another feature of the invention is that the amount of light received for a light path having a broadband source common to multiple light paths and a broadband detector common to multiple light paths can be independently monitored where at least one of the following occurs: a) between the source and the IRE, the path includes an optical filter of the determined frequency and an optical element that can be controlled to either allow light to pass or to be blocked in the path, b) between the detector and the IRE, the path includes an optical filter of the determined frequency and an optical element that can be controlled to either allow light to pass or to be blocked in the path, or c) combinations thereof.

Another feature of the invention is that the primary number of reflections that a light path makes from at least one convex surface of the IRE, which at can contact a fluid, is determined by at least one of the following: a) the shape of the IRE, b) a surface property of the IRE, c) the relative position at an IRE flat surface where the light path's IR source light enters the IRE, d) the relative position at an IRE flat surface where the light path's detector receives light that exits the IRE, or e) combinations thereof.

Another feature of the invention is that the shape of the IRE can be one of the following: a) essentially hemispherical, b) essentially a longitudinal rod section; and c) essentially a longitudinal tube section, and d) combinations thereof.

Another feature of the invention is that a surface property of the IRE can include at least one of the following: a) covering on a convex IRE surface, b) a discontinuity that transmits light out of the IRE separating convex surface sections, c) a discontinuity that reflects light in a direction that is not received by a detector separating convex surface sections that reflects light in a direction that is not received by a detector, d) a discontinuity that absorbs substantially all IR light separating surface sections, or e) combinations thereof.

Another feature of the invention is that a covering on a convex IRE surface can reflect a determined quantity of IR light essentially independent of a fluid in contact with the covering.

Another feature of the invention is that an IRE discontinuity is at least one of the following: a) at least one groove in the surface, b) surface roughening; c) changes in material property of the IRE, or e) combinations thereof.

Another feature of the invention is that the relative position where a light path enters the IRE is determined by one of the following: a) the mounting location of the source's output essentially adjacent to an IRE flat surface, or b) the mounting location of the output of an optical conduit communicating light from the source essentially adjacent to an IRE flat surface.

Another feature of the invention is that the relative position where a light path exits the IRE is determined by one of the following: a) the mounting location of the detector's input essentially adjacent to an IRE flat surface, or b) the mounting location of the input of an optical conduit communicating light to the detector, essentially adjacent to an IRE flat surface.

Another feature of the invention is that a light path can include at least one of the following: a) a lens between the source and the IRE to align light emitted from the source, b) a lens between the IRE and the detector to limit the angle of light exiting the IRE that can be received by the detector, or c) combinations thereof.

Another feature of the invention is that the electronics can include control means to independently monitor the amount of light received for each light path.

Another feature of the invention is that the electronics can use external control information to independently monitor the amount of light received for each light path.

Another feature of the invention is that the electronics can communicate the detector electrical output of each path as the information relevant to the monitored light reception.

Another feature of the invention is that the electronics can include means to convert detector electrical output of each path to suitable data and communicate those data as the information relevant to the monitored light reception.

Another feature of the invention is that electronics can include means to analyze the IR detector electrical output of each light path to determine a quality and/or condition of a fluid that can contact a convex surface of the IRE and communicate that determination as the information relevant to the monitored light reception.

Another feature of the invention is a process for on line monitoring of a fluid comprising:
- a) emitting light from at least one source to enter at least one essentially flat surface of an IRE,
- b) internally reflecting the light at least once from at least one convex surface of an IRE wherein the convex surface is in contact with a fluid and having the reflected light exit at least one essentially flat surface of the IRE,
- c) receiving at least a portion of the exiting light with at least one detector; and
- d) controlling light emitted from the source and the reflected light received by the detector such that at least two IR light paths of uniquely determined frequency are independently monitored, wherein the fluid quality and/or condition is being monitored.

Still other features of the present invention will become apparent to those of ordinary skill in the art upon reading and understanding the following detailed description of the preferred embodiments.

BRIEF DESCRIPTION OF THE DRAWINGS

FIG. 5 is a representative graph illustrating the IR characteristic of a premium quality fluid for a particular application and of a standard quality fluid for the same application.

FIG. 6 is a schematic illustration of a cross section of an invention embodiment where the number of reflection that a light path has with the IRE convex surface is determined by the IR detector position.

FIG. 7 is a schematic illustration of a cross section of an invention embodiment where the number of reflections that a light path has with the IRE convex surface is determined by the IR source position.

FIG. 8 is a schematic illustration showing an embodiment of the present invention with two IR light paths having independent detectors and a common source.

DETAILED DESCRIPTION OF THE invention

Figure 1:
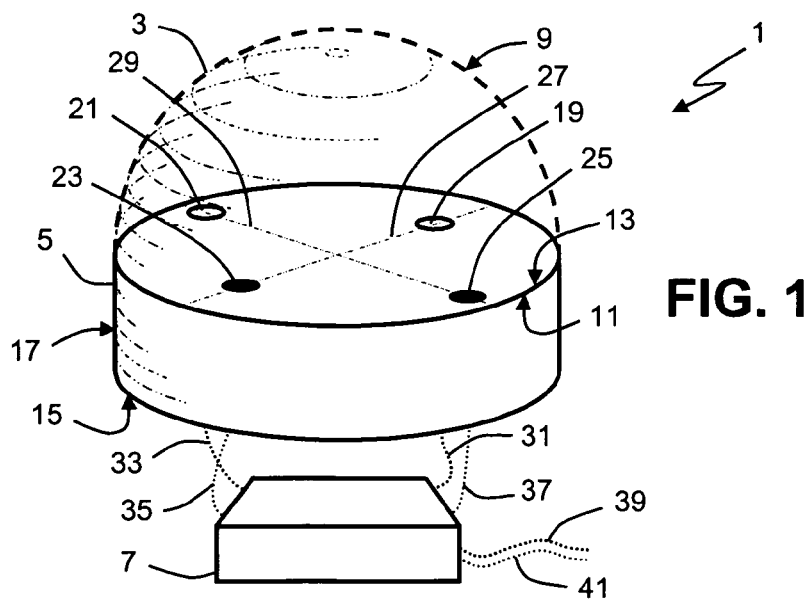
FIG. 1 is a schematic illustration showing an embodiment of the present invention with an essentially hemisphere IR-transparent internal-reflectance element (IRE) and with two IR light paths having independent sources and independent detectors.
Figure 2:
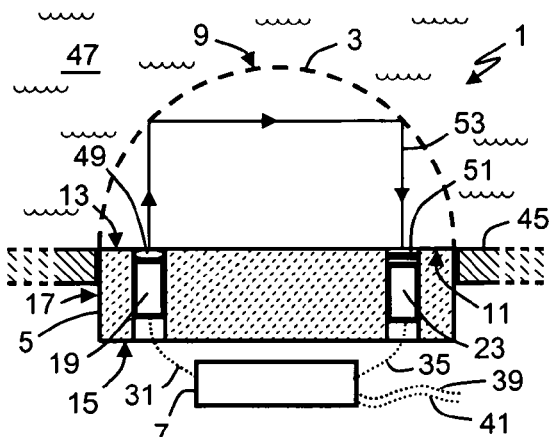
FIG. 2 is a schematic illustration of a cross section of the FIG. 1 apparatus showing a light path that has two reflections from the IRE convex surface.
Figure 3:
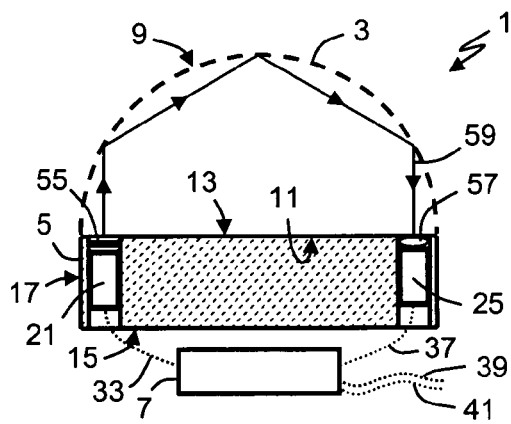
FIG. 3 is a schematic illustration of a cross section of the FIG. 1 apparatus showing a light path that has three reflections from the IRE convex surface.
Figure 4:
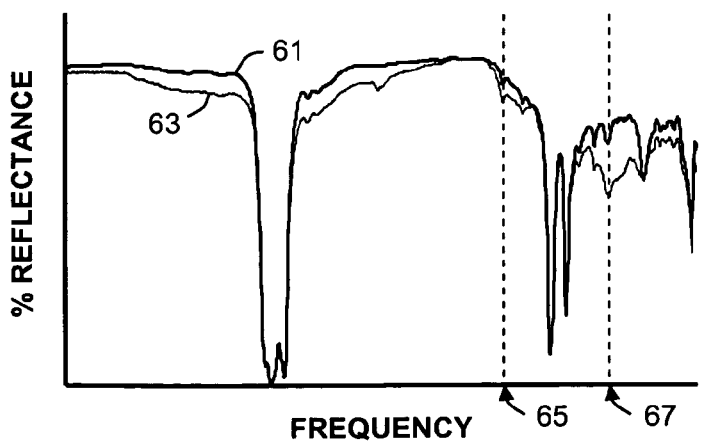
FIG. 4 is a representative graph illustrating the IR characteristic of a fresh fluid and of the same fluid after being deteriorated due to use.

FIG. 1 shows a schematic illustration of an on-line fluid monitoring apparatus in accordance with aspects of the present invention. Apparatus 1 includes an IR-transparent internal-reflectance-element (IRE) 3, mounting base 5 and electronics 7. IRE 3 is a solid of appropriate index-of-refraction that has essentially-hemispherical-shape convex surface 9 and essentially-flat surface 11. Base 5 is cylindrical in shape with upper-surface 13, lower surface 15 and side surface 17. Upper surface 13 of base 5 is fixedly attached to surface 11 of IRE 3. Side surface 17 of base 5 includes attachment means (not shown, but for example threads) that allows apparatus 1 to be mounted in a fluid container (not shown, but for example a fluid conduit or a reservoir) in a substantially leak free manner with fluid contacting surface 9 of IRE 3, but not contacting lower surface 15 of base 5 and electronics 7. Base 5 also includes two IR light sources 19; 21 and two IR light detectors 23, 25. In this and other figures showing schematic illustrations of invention embodiments in perspective, IR light sources are drawn as open ellipses and IR light detectors are drawn as filled ellipses. Also while shown as a single ellipse, a source can be comprised of one or more IR light emitters that are located together or separately, which are powered together as one, and a detector can be comprised of one or more IR light sensors that are located together or separately, which monitored together as one. IR Source 19 and detector 23, and other optical elements, which are shown in detail in FIG. 2, are fixedly held and located along a first diameter 27 (shown with phantom line) of base 5. Source 21 and detector 23, and other optical elements, which are shown in detail in FIG. 3, are fixedly held and located along a second diameter 29, which in one embodiment is essentially perpendicular to the first diameter 27, of base 5. Electronics 7 includes electronic circuitry needed to power IR sources 19, 21 through electrical conduits 31, 33 respectively, and to power, if necessary, and to receive detected IR light information from detectors 23, 25 through electrical conduits 35, 37 respectively. Electronics 7 is powered through electrical conduit 39 and communicates information with other devices (not shown) through electrical conduit 41.

Apparatus 1 can be configured such that electronics 7 include circuitry and software needed to control the powering of IR sources 19, 21 and analysis of detectors 23, 25 outputs for determining fluid quality/condition. If such circuitry and software are included in electronics 7, information needed for the analysis of particular fluids can be communicated to—and the output of the fluid quality/condition determination can be communicated from—electronics 7 by electrical conduit 41. Apparatus 1, however, need not include such control and data analysis circuitry and software. Electronics 7 can, through electrical conduit 41, receive information from—and communicate information to—other electronics (not shown) that provides the control and analysis functions.

FIG. 2 shows a schematic cross section of apparatus 1 of FIG. 1 where the apparatus is mounted in fluid reservoir 45 with fluid 47. Surface 17 of base 5 is mounted in a substantially leak free manner to reservoir 45 such that convex surface 9 of IRE 3 is in contact with fluid 47 and no fluid 47 is between IR sources 19, 21 (source 21 not shown) or IR detectors 23, 25 (detector 25 not shown) and flat surface 11 of the IRE (throughout this specification substantially leak free is as herein defined). The cross section is taken through diameter 27 of FIG. 1 such that broadband IR source 19 and IR detector 23 are shown. As previously described, source 19 is powered by electronics 7 through electrical conduit 31 and detector 23 communicates information to the electronics through electrical conduit 35. FIG. 2 further shows lens 49 between source 19 and flat surface 11 of IRE 3, and filter 51 between detector 23 and the IRE flat surface. Lens 49 aligns IR light emitted by source 19 so that in conjunction with the position of the source and the lens in base 5 and the shape of convex surface 9 of IRE 3 a substantial portion of the IR light emitted by the source is focused in a relatively small area along the same base diameter after making two reflections with the convex surface as shown by light ray 53. Filter 51 and detector 23 are positioned so that twice-reflected light of ray 53 from source 19 is filtered to a determined frequency, i.e. a determined central-frequency and determined bandwidth as previously discussed, before being received by the detector.

FIG. 3 shows a schematic cross section taken through diameter 29 of apparatus 1 shown in FIG. 1. IR source 21 and IR detector 25 are shown, and as previously described, broadband source 21 is powered by electronics 7 through electrical conduit 33 and broadband detector 25 is powered by—and communicates information to—electronics 7 through electrical conduit 35. FIG. 3 further shows filter 55 between source 21 and flat surface 11 of IRE 3, and lens 57 between detector 25 and the IRE flat surface. Filter 55 filters the IR light emitted by source 21 to a determined frequency. The filtered light from source 21 is sufficiently aligned so that in conjunction with the position of source and filter 55 in base 5 and the shape of convex surface 9 of IRE 3 a substantial portion of the light is focused in a relatively small area along the same base diameter after making three reflections with the convex surface as shown by light ray 59. Lens 57 and detector 25 are positioned so that the thrice-reflected filtered light of ray 59 from source 21 is received by the detector. Lens 57 allows light only from designed directions to reach detector 25.

To understand the operation of apparatus 1 of FIGS. 1, 2, and 3, FIG. 4 is a graph of representative IR characteristics of a fluid used in a transportation vehicle. The curves are percent reflectance as a function of frequency for IR light reflecting once from an IRE surface in contact with the fluid. A 100% reflectance at any given frequency means that no light is absorbed by the fluid when light is reflected from the IRE surface in contact with the fluid. The 100% reflectance value is the same as would be measured if a fluid were not contacting the IRE surface. A reflectance less than 100% is the amount of light at a given frequency that is not absorbed by a fluid in contact with the IRE surface when light is reflected at that surface. Curve 61 is the reflectance for an unused (new) fluid, and curve 63 is the reflectance of the same fluid that has been used and is close to the end of its useful life. Comparing curves 61, and 63, the changes in the chemical groups of the used fluid are shown at a multitude of frequencies; however in one fluid application, changes in the IR spectra at frequencies 65 and 67 are known to be of particular importance in determining fluid condition and predicting remaining fluid life. For that application, monitoring a fluid at frequencies 65, 67 during use would allow an operator, maintenance personnel or on-board diagnostics to determine when the most cost-efficient fluid replacement should occur. As the figure shows, the reflectance change at frequency 67 is small relative to the change at frequency 65, and depending on sensitivity of the detector and/or the resolution of the associated electronics monitoring reflectance change at frequency 67 as the fluid ages could be difficult. The relative change in the amount of light received at a detector can be increased for a relative change in a fluid's reflectance by increasing the number of reflections IR light makes with an IRE surface in contact with the fluid. In particular, the amount of light received at a detector as a function of the number of reflections N from an IRE surface in contact with the fluid is given by: $LN=AN \times BN$, where LN is the light received after N reflections, AN is the amount of light received after N reflections if no fluid is in contact with the IRE surface, B is the "single surface" percent reflectance of the fluid at the IR light frequency divided by 100, and BN is B raised to the Nth power. AN is essentially a constant since typically essentially 100% of the incident light is reflected from an IRE surface not in contact with a fluid. Hence, the relative change in the amount of light received at a detector is increased with increased number of reflections. Therefore, since the fluid shows relatively less change at frequency 67 than at frequency 65 as the fluid ages, a greater number of reflections at frequency 67 than at frequency 65 may allow better resolution of the change as the fluid ages.

FIG. 5 is an example of representative IR characteristics of fluids used in a transportation application. Curve 69 is the percent reflectance as a function of IR frequency for an unused premium quality fluid and curve 71 is the percent reflectance as a function of frequency for an unused standard quality fluid. Comparing curves 69, 71, the differences at a multitude of frequencies correspond to a multitude of differences in particular chemical groups of the two fluids. Of particular interest in determining the overall quality of the fluids, however, are differences in IR reflectance at frequencies 73, 75. The chemical groups responsible for differences at these two frequencies distinguish the premium from the standard fluid. Since the fluid change cycle and, in some cases, equipment performance limits are set based on fluid quality, information about fluid quality is needed by the operator, the maintenance personnel or the on-board diagnostics. As the figure shows, the relative reflectance difference between the fluids at frequency 75 is greater than at frequency 73. Again as described in the discussion of FIG. 4, depending on the sensitivity of detectors and/or resolution of electronics, the fluid may be quality of the fluids shown in FIG. 5 may be more effectively monitored where there are a greater number of IRE surface reflection at frequency 73 than at frequency 75.

Referring to FIGS. 1, 2, 3, apparatus 1 is designed for an application where at filter 51 frequency two IRE 3 reflections and at filter 55 frequency three IRE 3 reflections are sufficient to monitor fluid change and/or quality. For example, apparatus 1 could be designed for use in determining the condition of the fluid shown in FIG. 4 where filter 51 has frequency 65 and filter 55 has frequency 67. As another example, apparatus 1 could be designed for use in determining the quality of the fluid shown in FIG. 5 where filter 51 has frequency 75 and filter 55 has frequency 73. In apparatus 1 operation, power is applied to electronics 7 through electrical conduit 39 and either a controller in the electronics or information from an external controller is communicated to the electronics, through electrical conduit 41, determines when to apply power to IR sources 19, 21. If sources 19, 21 are sufficiently small, the emitted light sufficiently aligned, the sources and the detectors 23, 25 appropriately positioned, and IRE 3 appropriately shaped and optically substantially defect-free, then power may be applied simultaneously to sources 19, 21. However, even small variations in one of the above variables can substantially affect the focus of light from sources 19, 21 on detectors 23, 25 respectively. Since unfiltered light from source 19 that reaches unfiltered detector 25 through lens 57 will be received in addition to the filtered light from source 21, the reflectance of IR light at the filter 55 frequency may not be able to be independently determined if both light sources are powered simultaneously. Apparatus 1 may be more appropriately controlled to power one source and monitor the respective detector sequentially, repeating the sequence for continuous operation, to assure independent monitoring of the IR light reflectance at the uniquely determined filter 51, 55 frequency of each path.

As an independent light path when source 19 is powered, a significant portion of the emitted light is reflected twice from surface 9 of IRE 3, as shown by light ray 53, and filtered and received by detector 23. The amount of light received at detector 23 when no fluid is in contact with surface 9 of IRE 3 is essentially 100% reflectance of the filter 51 frequency light from source 19. The amount of light received at detector 23 when fluid is in contact with surface 9 is approximately the 100% reflectance amount times the square of the fluid's percent reflectance at filter 51 frequency for one reflection divided by 100 {i.e. light received=100% reflectance×(percent reflectance at filter 51 frequency/100) 2}. The detected light is only approximately proportional to the single-surface-reflectance squared due to size, position, alignment, shape and other issues with apparatus 1 components, which may cause a portion of the light emitted by the source 19 to be reflected more than twice from surface 9 of IRE 3 before being received by detector 23. Thus, detected light may have terms with higher than second order in single-surface-reflectance. Nonetheless, a relatively exact equation can be calculated or an empirical curve can be fit that allows a fluid's single-surface-reflectance at filter 51 frequency to be determined from the light received at detector 23 while source 19 is powered. Such a determination can be made within electronics 7 or by a signal processor external to apparatus 1.

Similarly, as an independent light path when source 21 is powered, a significant portion of the emitted light, filtered by filter 55, is reflected thrice from surface of IRE 3, as shown by light ray 59, and received by detector 25. The amount of light received at detector 25 when no fluid is in contact with surface 9 of IRE 3 is essentially 100% reflectance of the filter 55 frequency light from source 21. The amount of light received at detector 25 when fluid is in contact with surface 9 is approximately the 100% reflectance amount times the cube of the fluid's percent reflectance at filter 55 frequency for one reflection divided by 100 {i.e. light received=100% reflectance×(percent reflectance at filter 55 frequency/100) 3}. The detected light is only approximately proportional to the single-surface-reflectance cubed due to size position, alignment, shape and other issues with apparatus 1 components, which may cause a portion of the light emitted by the source 21 to be reflected only twice or more than three times from surface 9 of IRE 3 before being received, even with lens 57 rejecting most off-axis light, at detector 25. Thus, detected light may have terms of order lower and higher order than three in single-surface-reflectance. Nonetheless, a relatively exact equation can be calculated or an empirical curve can be fit that allows a fluid's single-surface-reflectance at filter 55 frequency to be determined from the light received at detector 25 while source 21 is powered. Such a determination can be made within electronics 7 or by a signal processor external to apparatus 1.

Electronics 7 of apparatus 1 uses the monitored outputs of detectors 23 and 25 when sources 19, 21 respectively are powered to analyze the condition and/or quality of a fluid in contact with surface 9 of IRE 3 and communicates the results of the analysis through electrical conduit 41. In other embodiments, electronics 7 can communicate the unmodified outputs of detectors 23, 25 for processing external to apparatus 1, can communicate signals, for examples 0–5V or 4–20 mA signals, that the electronics determines as a function of detectors 23, 25 outputs, or can communicate other relevant information determined or calculated by the electronics. In any case, electronics 7 of apparatus 1 communicates information through electrical conduit 41 that is relevant to independently monitored outputs of detectors 23 and 25.

While the invention as embodied in FIGS. 1, 2, and 3 shows only two filtered light paths with separate IR source, IR detector and filter for determining a fluid's condition and/or quality, the apparatus can have more than two light paths. When there are more than two light paths, some of the light paths can be redundant such that they monitor the same filtered frequency. There must, however, be at least two light paths that can be independently monitored to determine light reflectance at different frequencies.

While the embodiment of FIGS. 1, 2, and 3 shows filter 51 between detector 23 and surface 11 of IRE 3 for one light path, and with filter 55 between source 21 and surface 11 of IRE 3 for the other light path, other embodiments can have both light paths with filters between their respective sources and the IRE or between their respective detectors and the IRE. Also another embodiment can have a source that only emits light and/or a detector that only detects light at the light path's unique frequency instead of using a filter in one or both light paths. In embodiments where both light paths have filters between their respective detectors and the IRE or have detectors that can only receive light at unique frequencies, the two light paths can be monitored independently even if both sources are emitting light simultaneously.

While the embodiment of FIGS. 1, 2, and 3 shows lens 49 between source 19 and surface 11 of IRE 3 for one light path, and lens 57 between detector 25 and surface 11 of IRE 3 for the other light path, other embodiments can have both light paths with lenses between sources and the IRE and/or between detectors and the IRE, or can have no lens external to the sources or detectors.

While the embodiment of FIGS. 1, 2, and 3 shows one light path with primarily two reflections on surface 9 of IRE 3 and one light path with primarily three reflections, other embodiments can have two light paths with the same number of primary reflections, and/or can have light paths designed with greater than three reflections in the IRE.

While the embodiment of FIGS. 1, 2, and 3 shows electronics 7 of apparatus 1 independent of base 5, the apparatus may be package to have the base with IRE 3 and the electronics within a single unit. Packaging is not critical other than in terms of the operation and function described, and is typically determined by cost and size constraints of the particular apparatus application.

In the embodiment shown in FIGS. 1, 2, and 3, the primary number of reflections made by light paths from surface 9 of IRE 3 is determined both by the position of the outputs of respective sources 19, 21 and the inputs of respective detectors 23, 25 relative to the flat IRE surface 13. The primary number of reflections that a light path makes in an IRE, however, can be determined by the position of only either the source output or the detector input.

FIG. 6 shows a schematic cross section of another embodiment of the invention. Apparatus 77 is similar to the cross section of apparatus 1 shown in FIG. 2 and similar features are labeled the same. Apparatus 81 includes IRE 3, mounting base 5 and electronics 7. IRE 3 is essentially a hemisphere (shown in cross section as a semi-circle) with convex surface 9 and flat surface 11. Upper surface 13 of base 5 is fixedly attached to surface 11 of IRE 3. Side surface 17 of base 5 is designed so that apparatus 77 can be mounted (by means not shown) in a fluid container (not shown) in a substantially leak free manner with fluid contacting surface 9 of IRE 3, but not contacting lower surface 15 and electronics 7. Base 5 includes IR detector 79, which receives light only of a unique frequency and is powered by (if necessary) and communicates information to electronics 7 through electrical conduit 81. Detector 79 is positioned in base 5 so to receive twice reflected light from light ray 53. Base 5 also includes broadband IR light source 83 that can be powered through electrical conduit 85 from electronics 7. Unlike IR light source 19 of FIG. 2, which is of relatively small size so that a majority of the emitted light reflects only twice from surface 9 of IRE 3 before reaching surface 13 of the IRE, IR light source 83 is of sufficient size that not only does a portion of the emitted light reflect twice as shown by light ray 53, but a portion of the emitted light reflects greater than twice before reaching surface 13, for example three times as shown by light ray 59. In this embodiment placement, only the placement of unique frequency detector 79 determines that the light path, which includes the detector and source 83, has primarily the two reflections of ray 53.

In use, source 83 of apparatus 77 emits sufficient IR light when powered through electrical conduit 85 such that the amount of light received at the detector 79 frequency is sufficient to measure changes as the fluid in contact with surface 9 of IRE 3 changes. The amount of light received at detector 79 if no fluid is in contact with surface 9 of IRE 3 is essentially 100% reflectance of the detector-frequency light from source 83. The amount of light received at detector 79 when fluid is in contact with surface 9 is approximately the 100% reflectance amount times the square of the fluid's percent reflectance at the detector frequency for one reflection divided by 100 {i.e. light received=100% reflectance×(percent reflectance at detector 79 frequency/100)2}. The received light is only approximately proportional to the single-surface-reflectance squared due to size, position, alignment, shape and other issues with apparatus 77 components. In particular, the size of source 83 increases the probability that a portion of the light emitted by the source is reflected more than twice from surface 9 of IRE 3 before being received by detector 79. Thus, detected light may have terms with higher than second order in single-surface-reflectance. Nevertheless, the variables are still sufficiently well defined and can be controlled so that a relatively exact equation can be calculated or an empirical curve can be fit that allows a fluid's single-surface-reflectance at detector 79 frequency to be determined from the light received at the detector while source 83 is powered. In any case, electronics 7 of apparatus 77 communicates information through electrical conduit 41 that is relevant to light received at detector 79.

FIG. 7 shows a schematic cross section of another embodiment of the invention. Apparatus 87 is similar to the cross section of apparatus 1 shown in FIG. 3 and similar features are labeled the same. Apparatus 87 includes IRE 3, mounting base 5 and electronics 7. IRE 3 is essentially a hemisphere (shown in cross section as a semi-circle) with convex surface 9 and flat surface 11. Upper surface 13 of base 5 is fixedly attached to surface 11 of IRE 3, and base side surface 17 is designed to allow apparatus 91 to be mounted (by means not shown) in a fluid container (not shown) in a substantially leak free manner with fluid contacting surface 9 of the IRE, but not contacting base lower surface 15 and electronics 7. Base 5 includes IR light source 89, which emits light only at a unique frequency and is powered by electronics 7 through electrical conduit 91. Source 89 is positioned in base 5 so that when powered, a significant portion of the emitted light is reflected thrice from surface 9 of IRE 3 before reaching surface 13 of the IRE as shown by light ray 59. Base 5 also includes IR light detector 93 that is powered by (if necessary) and communicates information to electronics 7 through electrical conduit 95. Unlike detector 25 of FIG. 3, which is of relatively small size and positioned to primarily receive only light that is thrice reflected from surface 9 of IRE 3, detector 93 is of sufficient size and positioned to receive thrice reflected light, as shown by ray 59, but also light reflected a number of times other than three, for example two as shown by light ray 55. In this embodiment, only the placement of unique frequency source 89 determines that the light path, which includes the source and detector 93, has primarily the three reflections of ray 59.

In use, when powered through electrical conduit 91, the unique frequency light emitted by source 89 of apparatus 87 is received by detector 93, which is of sufficient sensitivity to measure changes as fluid in contact with surface 9 of IRE 3 changes. The amount of light received at detector 93 if no fluid is in contact with surface 9 of IRE 3 is essentially 100% reflectance of the source 89 frequency light. The amount of light received at detector 93 when fluid is in contact with surface 9 is approximately the 100% reflectance amount times the cube of the fluid's percent reflectance at source 89 frequency for one reflection divided by 100 {i.e. light received=100% reflectance×(percent reflectance at source 89 frequency/100)3}. The detected light is only approximately proportional to the single-surface-reflectance cubed due to size, position, alignment, shape and other issues with apparatus 87 components. In particular, the size of detector 93 increases the probability that a portion of the light received from source 89 is reflected other than thrice from surface 9 of IRE 3. Thus, detected light may have terms with other than third order in single-surface-reflectance. Nevertheless, the variables are sufficiently still well defined and can be controlled so that a relatively exact equation can be calculated or an empirical curve can be fit that allows a fluid's single-surface-reflectance to be determined from the light received at detector 93 while source 89 is powered. In any case, electronics 7 of apparatus 87 communicates information through electrical conduit 41 that is relevant to the light received from source 89.

The invention embodiments shown in FIGS. 1, 2, 3, 6, and 7 each light path has independent sources and detectors, and the sources and detectors are mounted in close proximity, essentially adjacent, to flat surface 11 of IRE 3. Each light path, however, does not need independent sources and/or detectors, and sources and/or detectors do not need to be mounted in close proximity to an IRE surface.

FIG. 8 is a schematic illustration of another embodiment of the present invention where the same components as those of apparatus 1 in FIG. 1 are labeled the same. Shown is apparatus 101 that includes IRE 3, mounting base 5 and electronics 7. IRE 3 has convex surface 9 and essentially flat surface 11. Base 5 has flat upper-surface 13, lower surface 15 and side surface 17. Upper surface 13 of base 5 is fixedly attached to surface 11 of IRE 3, and base side surface 17 apparatus 101 to be mounted in a fluid container in a substantially leak free manner so that fluid contacts surface 9 of IRE 3 without contacting the base lower surface 15 or electronics 7. Base 5 includes a single broadband IR light source 103 and optical conduits 105, 107 with ends 109, 111 respectively positioned at surface 11. Optical conduits 105, 107 terminate external to the base 5 at unique frequency filters 113, 115 respectively at inputs to IR detectors 117 and 119 respectively. Electronics 7 includes electronic circuitry needed to power IR source 103 through electrical conduit 121, and to power, if necessary, and to receive IR light information from detectors 117, 119 through electrical conduits 123, 125 respectively. Electronics 7 is powered through electrical conduit 39, and communicates information with other apparatus (not shown) through electrical conduit 41.

In operation, power is applied to electronics 7 of apparatus 101 through electrical conduit 39. Since apparatus 101 has only one IR light source 103, the source can be powered when power is applied to electronics 7 through conduit 39 or can be powered when determined by either a controller in the electronics or information communicated through electrical conduit 41 from an external controller. In any case, when source 103 is powered, light is reflected from surface 9 or IRE 3, received by ends 109, 111, communicated through optical conduits 105, 107 respectively and filters 113, 115 respectively, and received by detectors 117, 119 respectively. The position of end 109 determines the number of reflections that the light path, which includes source 103, filter 113 and detector 117, makes from surface 9 of IRE 3. The position of end 111 determines the number of reflection that the light path, which includes source 103, filter 115 and detector 119, makes from surface 9 of IRE 3. The amount of light received at detectors 117, 119 if no fluid is in contact with surface 9 of IRE 3 is essentially 100% reflectance of filter 113 frequency and filter 115 frequency respectively. The amount of light received at detectors 117, 119 when a fluid is in contact with surface 9 of IRE 3 is a function of the positioning of ends 109, 111 respectively and the single-surface-reflectance of the fluid at filter frequencies 113, 115 respectively. With the positions of ends 109, 111 fixed in base 5, relatively exact equations can be calculated or empirical curves can be fit that allow a fluid's single-surface-reflectance at the filter 113, 115 frequencies to be determined from the light received at detectors 117, 119 respectively while source 103 is powered. In any case, electronics 7 of apparatus 101 communicates information relevant to light received at detectors 117, 119 through electrical conduit 41.

While FIG. 8 shows an invention embodiment with two light paths having a single broadband IR light source, other embodiments can have a greater number of light paths with the same source. Also an invention embodiment can have more than one light source where one or more of the sources provide the light for more than one light path. The light sources, however, must be able to be controlled such that the at least two light paths with uniquely determined frequency can be monitored independent of other paths.

While FIG. 8 shows filters for determining each light path's unique frequency, another embodiment can have light paths with detectors that only receive light of the desired unique frequency.

The embodiment shown in FIG. 8 has light paths with common source and independent detectors. The present invention can also have light paths with common detector and independent sources.

Figure 9:
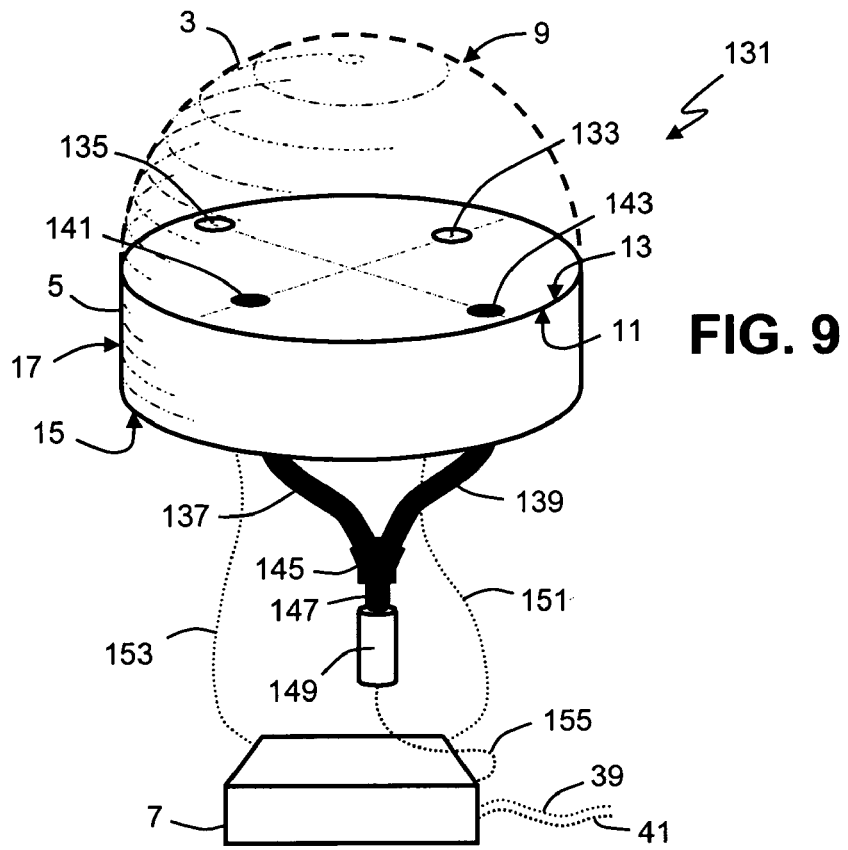
FIG. 9 is a schematic illustration showing an embodiment of the present invention with two IR light paths having independent sources and a common detector.

FIG. 9 is a schematic illustration of another embodiment of the present invention where components that are the same as those in the embodiment of FIG. 1 are labeled the same. Shown is apparatus 131 that includes IRE 3, mounting base 5 and electronics 7. IRE 3 has convex surface 9 and essentially flat surface 11. Base 5 has flat upper-surface 13, lower surface 15 and side surface 17, with upper surface 13 fixedly attached to surface 11 of IRE 3, and side surface 17 allowing apparatus 131 to be mounted substantially leak free in a fluid container as previously described. Base 5 includes IR light sources 133, 135, which each emit a unique frequency, and optical conduits 137, 139 with ends 141, 143 respectively at surface 13. Light sources 133, 135 and ends 141, 143 of respective optical conduits 137, 139 are positioned so that light from source 133 reflects a determined number of times from convex surface 9 of IRE 3 before being received by the end 141, and light from light source 135 reflects an independently determined number of times from surface 9 of IRE 3 before being received by the end 143. Optical conduits 137, 139 terminate at optical coupler 145 which combines the conduits' outputs into one optical conduit 147 for communication to light detector 149. That is detector 153 receives light from both inputs 141, 143. Electronics 7 includes electronic circuitry needed to power IR sources 133, 135 through electrical conduits 151, 153 respectively, and to power, if necessary, and to receive IR light information from detector 149 through electrical conduit 155. Electronics 7 receives power through electrical conduit 39 and communicates information with other apparatus (not shown) through electrical conduit 41.

In operation, power is applied to electronics 7 of apparatus 131 through electrical conduit 39. Electronics 7 applies power to sources 133, 135 when determined by a controller in the electronics or by information communicated through electrical conduit 41 from an external controller. Since light from both unique frequency sources 133, 135 is received by the single detector 149, to operate the light path defined by unique frequency source 133, and detector 149 independently from the light path defined by unique frequency source 135, and detector 149, apparatus 131 is controlled to power one source at a time and to identify the information received by detector 149 by which source is powered at the time. That is, when source 133 is powered and source 135 is not powered, the light received by detector 149 contains information about the single-surface-reflectance at source 133 frequency of a fluid in contact with surface 9 of IRE 3, and when source 135 is powered and source 133 is not powered, the light received by detector 149 contains information about the single-surface-reflectance at source 135 frequency of a fluid in contact with the IRE convex surface. As in other embodiments, if no fluid is in contact with surface 9 of IRE 3, the amount of light received at detector 149 is 100% reflectance of source 133 frequency when source 133 is powered and source 135 not powered, and is the amount of light received at detector 149 is 100% reflectance of source 135 frequency when source 135 is powered and source 133 is not powered. The amount of light received at detector 149 for the same two cases when a fluid is in contact with surface 9 of IRE 3 is a function of the positioning of the source 133 or 135 and the end 141 or 143 of the respective optical conduits 137, or 139, and the fluid's single-surface-reflectance at the source 133 or 135 frequency of the particular light path that is powered. Electronics 7 of apparatus 131 communicates information relevant to the light received at detector 149 through electrical conduit 41.

While FIG. 9 shows an invention embodiment with two light paths having a single IR light detector, other embodiments can have a greater number of light paths with the same detector. Also an invention embodiment can have more than one detector where one or more of the detectors are used in multiple light paths. In such an embodiment, however, the light sources must be able to be controlled such that the light paths with uniquely determined filter frequency can be independently monitored for IR light reflectance.

While the embodiment of FIG. 9 is described with each light path's unique frequency determined by a light source that only emits light at that unique frequency, another embodiment can have light paths which have a broadband light source and a filter of unique frequency between the source and that IRE to determine a light path's unique frequency.

FIG. 8 shows light paths with common source and independent detectors, and FIG. 9 shows light paths with common detector and independent sources. The present invention can also have light paths with common source and common detector.

Figure 10:
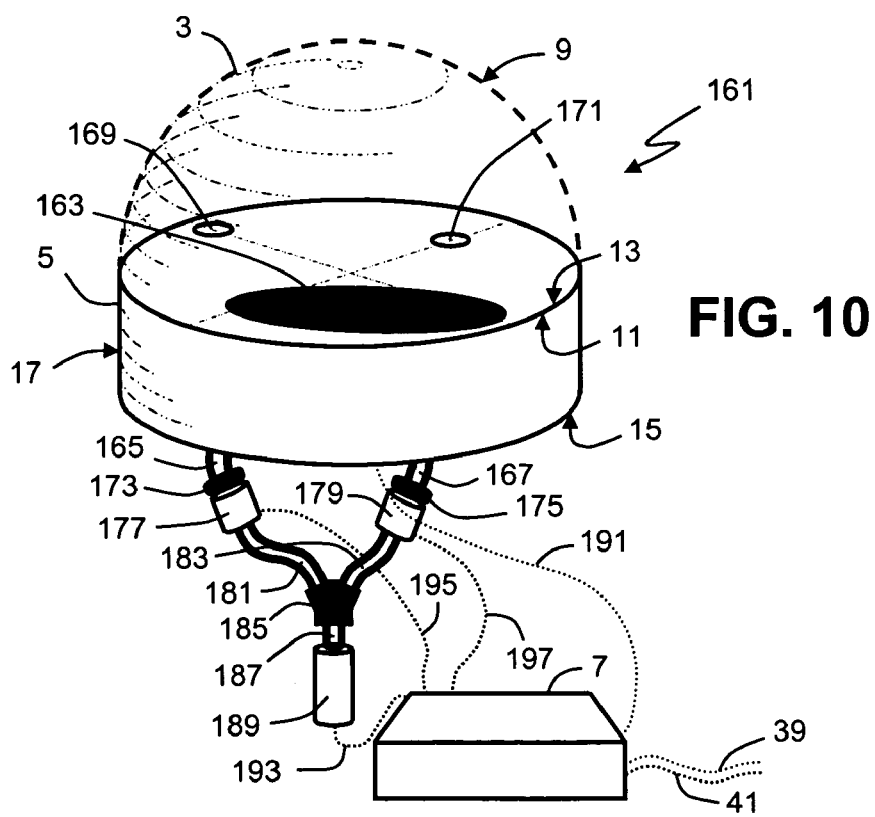
FIG. 10 is a schematic illustration showing an embodiment of the present invention with two IR light paths having common source, common detector and electrically controlled means between the source and the IRE that allows the independent monitoring of light reflectance of each path.

FIG. 10 is a schematic illustration of another embodiment of the present invention where components that are the same as those in the embodiment of FIG. 1 are labeled the same. Shown is apparatus 161 that includes IRE 3, mounting base 5 and electronics 7. IRE 3 has convex surface 9 and essentially flat surface 11. Base 5 has flat upper-surface 13, lower surface 15 and side surface 17, with upper surface 13 fixedly attached to IRE 3 surface 11 and with side surface 17 allowing apparatus 161 to be mounted substantially leak free in a fluid container as previously described. Base 5 includes a large-area single IR light detector 163 and optical conduits 165, 167 with ends 169, 171 respectively positioned at surface 13 to determine the number of reflections that light emitted from the conduit ends makes in IRE 3 before being received by detector 163. Optical conduits 165, 167 are components of optical circuits that also include unique frequency filters 173, 175 respectively, electro-optical elements 177, 179 respectively, optical conduits 181, 183 respectively, optical splitter 185, optical conduit 187 and IR light source 189. Elements 177, 179 are optical devices that are electrically controlled to either allow light to pass through or be blocked by the element. Elements 177, 179, for example, can be electrically-controlled, normally-closed mechanical shutters that open when power is applied, or, as another example, can be normally-optically-opaque materials that become IR transparent when power is applied. Electronics 7 includes electronic circuitry needed to power, if necessary, and to receive IR light information from detector 193 through electrical conduit 191, to power IR source 189 through electrical conduit 193, and to power electro-optical elements 177, 179 through electrical conduits 195, 197 respectively. Electronics 7 receives power through electrical conduit 39 and communicates information with other apparatus (not shown) through electrical conduit 41.

In operation, power is applied to electronics 7 of apparatus 161 through electrical conduit 39. Since there is only one IR source 189, power can be applied to the source when electronics 7 is powered, or the source can be powered when determined by a controller in the electronics or by information communicated through electrical conduit 41 from an external controller (not shown). Emitted light from source 189 is communicated through optical conduit 187 to splitter 185 which communicates approximately 50% of the light to each optical conduit 181, 183 and electro-optical elements 177, 179 respectively. When the appropriate power is applied by electronics 7 to electro-optical element 177, light from source 189 passes through the element, filter 173 and optical conduit 165, and out end 169 where the light of filter 173 frequency reflects a designed number of times from surface 9 of IRE 3 before being received by detector 163. Similarly when appropriate power is applied by electronics 7 to electro-optical element 179, light from source 189 passes through the element, filter 175 and optical conduit 167, and out end 171 where the light of filter 175 frequency reflects a designed number of times from surface 9 of IRE 3 before being received by detector 163. Since the filtered light from both ends 169, 171 is received by the single detector 163, to operate the light path defined by source 189, filter 173 and detector 163 independent of the light path defined by source 189, filter 175 and detector 163, apparatus 161 is controlled to power electro-optical elements 177, 179 such that light passes through only one element at a time and to identify the information received by detector 163 by which element is allowing light to pass at the time. That is, when element 177 is powered to allow light to pass and element 179 is powered to block light, the light received by detector 163 contains information about the single-surface-reflectance at filter 173 frequency of a fluid in contact with surface 9 of IRE 3, and when element 179 is powered to allow light to pass and element 177 is powered to block light, the light received by detector 163 contains information about the single-surface-reflectance at filter 175 frequency of a fluid in contact with the IRE convex surface. If no fluid is in contact with surface 9 of IRE 3, the amount of light received at detector 163 is 100% reflectance of filter 173 frequency when element 177 allows light through and element 179 blocks light, and the amount of light received at detector 163 is 100% reflectance of filter 175 frequency when element 179 allows light through and element 177 blocks light. The amount of light received at detector 163 for the same two cases when a fluid is in contact with surface 9 of IRE 3 is a function of the positions of end 169 or 171 of optical conduits 165 or 167 respectively, and the fluid's single-surface-reflectance at the filter 173 or 175 frequency of the particular light path that has the element 177 or 179 powered to allow light to pass. Electronics 7 of apparatus 161 communicates information relevant to the light received at detector 163 through electrical conduit 41.

While FIG. 10 shows two light paths having common IR light source and detector, another embodiment can have a greater number of light paths with common source and detector. Also other embodiments can have more than one source and/or more than one detector common to multiple light paths as long as light paths with uniquely determined filter frequency can be controlled for independent monitoring the light received for each light path.

Figure 11:
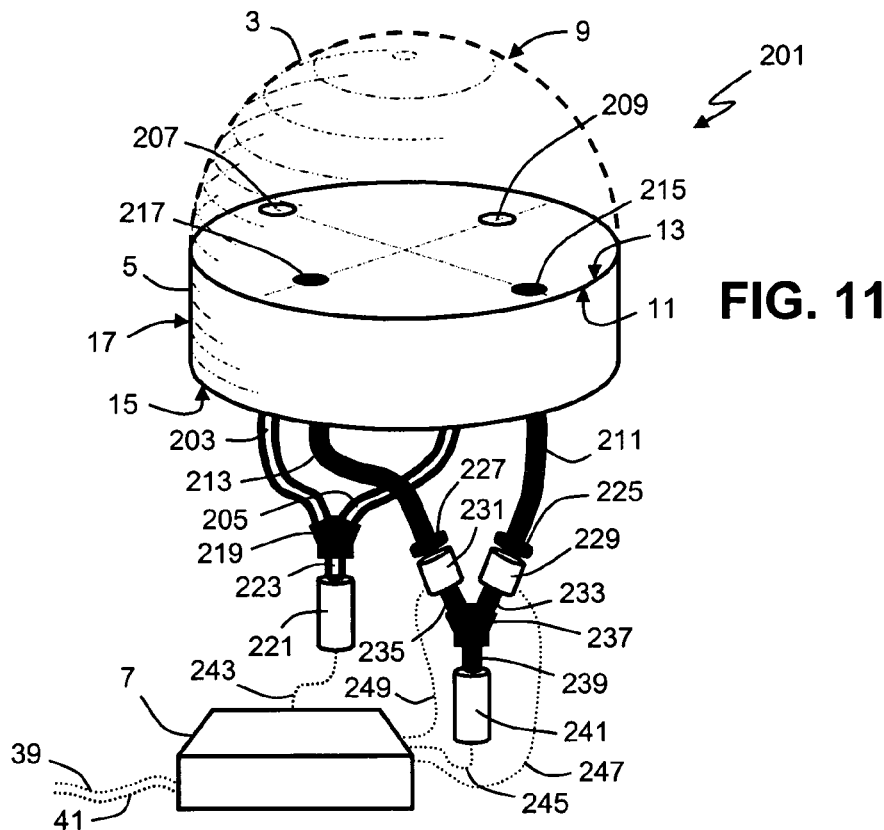
FIG. 11 is a schematic illustration showing an embodiment of the present invention with two IR light paths having common source, common detector and electrically controlled means between the detector and the IRE that allows the independent monitoring of light reflectance of each path.

FIG. 11 is a schematic illustration of another embodiment of the present invention with two light paths having common source and common detector. Shown is apparatus 201 that includes IRE 3, mounting base 5 and electronics 7. IRE 3 has convex surface 9 and essentially flat surface 11. Base 5 has flat upper-surface 13, lower surface 15 and side surface 17, upper surface 13 fixedly attached to IRE 3 flat surface 11 and with side surface 17 allowing apparatus 201 to be mounted substantially leak free in a fluid container as previously described. Base 5 includes optical conduits 203, 205 with ends 207, 209 respectively positioned at surface 13, and optical conduits 211, 213 with ends 215, 217 respectively positioned at surface 13. The positioning of ends 207, 215 along one diameter of surface 11 determine the number of reflections made in IRE 3 for one light path of apparatus 201, and the positioning of ends 209, 217 along another diameter of surface 11 determine the number of reflections made in IRE 3 for the other light path of the apparatus. Optical conduits 203, 205 terminate at optical splitter 219 which receives IR light from source 221 through optical conduit 223. Optical conduits 211, 213 are components of optical circuits that also include unique frequency filters 225, 227 respectively, electro-optical elements 229, 231 respectively, optical conduits 233, 235 respectively, optical coupler 237, conduit 239 and IR light detector 241. Elements 229, 231 are optical devices that are electrically controlled to either allow light to pass through or be blocked by the elements; for example the elements can be electrically-controlled, normally-open, mechanical shutters that close when power is applied, an another example the elements can be normally-IR-transparent material that becomes IR-opaque when power is applied, or the like. Optical coupler 237 combines output from conduits 233, 235 into one conduit 239 for communication to light detector 241. Electronics 7 includes electronic circuitry needed to power IR source 223 through electrical conduit 243, to power, if necessary, and to receive IR light information from detector 241 through electrical conduit 245, and to power electro-optical elements 223, 235 through electrical conduits 247, 249 respectively. Electronics 7 receives power through electrical conduit 39 and communicates information with other apparatus (not shown) through electrical conduit 41.

In operation, power is applied to electronics 7 of apparatus 201 through electrical conduit 39. Since there is only one IR source 221, power can be applied to the source when electronics 7 is powered, or the source can be powered when determined by a controller in the electronics or by information communicated through electrical conduit 41 from an external controller (not shown). Emitted light from source 221 is communicated through optical conduit 223 to splitter 219 which communicates approximately 50% of the light through each optical conduit 203, 205 to ends 207, 209 respectively where the light is emitted into IRE 3, reflected a designed number of times from convex surface 9 and received at ends 215, 217 respectively of optical conduits 211, 213 respectively. Light received by optical conduit 211 passes through filter 225 and when the appropriate power is applied by electronics 7 to electro-optical element 229, the light passes through optical conduit 233, coupler 237 and conduit 239, and is received by detector 241. Similarly, light received by optical conduit 213 passes through filter 227 and when the appropriate power is applied by electronics 7 to electro-optical element 231, the light passes through optical conduit 235, coupler 237 and conduit 239, and is received by detector 241. Since the filtered light from both ends 215, 217 is received by the single detector 241, to operate the light path defined by source 221, filter 225 and detector 241 independently from the light path defined by source 221, filter 227 and detector 241, apparatus 201 is controlled to power the electro-optical elements 229, 231 such that light passes through only one element at a time and to identify the information received at detector 241 by which element is allowing light to pass at the time. That is, when element 229 is powered to allow light to pass and element 231 is powered to block light, the light received by detector 241 contains information about the single-surface-reflectance at filter 225 frequency of a fluid in contact with surface 9 of IRE 3, and when element 231 is powered to allow light to pass and element 229 is powered to block light, the light received by detector 241 contains information about the single-surface reflectance at filter 227 frequency of the fluid in contact with the IRE convex surface. If no fluid is in contact with surface 9 of IRE 3, the amount of light received at detector 241 is 100% reflectance of filter 225 frequency when element 229 allows light through and element 231 blocks light, and the amount of light received at detector 241 is 100% reflectance at filter 227 frequency when element 231 allows light through and element 229 blocks light. The amount of light received at detector 241 for the same two cases when fluid is in contact with surface 9 of IRE 3 is a function of the positions of ends 207, 215 of optical conduits 203, 211 respectively, and ends 209, 217 of optical conduits 205, 213 respectively, and the fluid's single-surface-reflectance at the filter 225 or 227 frequency of the particular light path that has the element 229 or 231 powered to allow light to pass. Electronics 7 of apparatus 201 communicates information relevant to the light received at detector 241 through electrical conduit 41.

While FIG. 11 shows an embodiment with two light paths having common IR light source and detector where the optical conduits are used to communicate light from the source and an essentially flat IRE surface, and from an essentially flat IRE surface and the detector, other embodiments can have a greater number of light paths with common source and detector. Also invention embodiments can have more than one source and/or more than one detector common to multiple light paths as long as the light paths, with uniquely determined filter frequency, can be controlled for independent monitoring of IR light reflectance.

IRE 9 of the embodiments of the invention shown and described thus far has an essentially hemispherical-shaped convex surface. The convex IRE surface for the present invention, however, does not have to be hemispherical-shaped.

Figure 12:
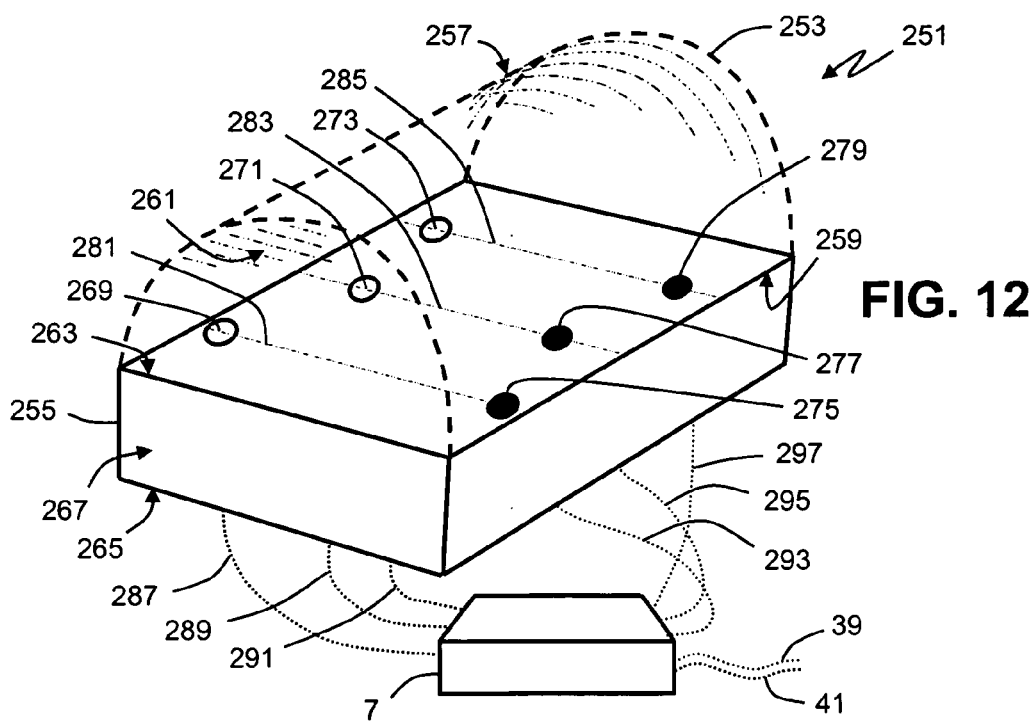
FIG. 12 is a schematic illustration showing an embodiment of the present invention with an essentially longitudinal-rod-section shaped IRE and with three IR light paths having independent sources and independent detectors.

FIG. 12 shows a schematic illustration of an on-line fluid monitoring apparatus of the present invention. Apparatus 251 includes IR transparent IRE 253, mounting base 255 and electronics 7. IRE 253 is a solid of appropriate index-of-refraction with a shape that is essentially a section of a cylinder cut along the cylinder axis and that includes convex surface 257, essentially-flat surface 259 and two ends generally labeled 261. Base 255 has essentially-flat upper surface 263, lower surface 265 and side surfaces generally labeled 267. Upper surface 263 of base 255 is fixedly attached to surface 259 of IRE 253. Although not shown, side surfaces 267 of base 5 include attachment means or are incorporated in a package that has attachment means that allows apparatus 251 to be mounted in a fluid container in a substantially leak free manner with fluid contacting surface 257 of IRE 253, but not contacting lower surface 265 of base 255 and electronics 7. Base 255 includes three broadband IR light sources 269, 271, 273 and three unique frequency IR light detectors 275, 277, 279. Source 269 and detector 275 are fixedly held and located in base 255 along what is essentially a first diameter 281 (shown with phantom line) of IRE 253, source 271 and detector 277 are fixedly held and located along a second diameter 283, and source 273 and detector 279 are fixed held and located along a third diameter 285. Electronics 7 includes electronic circuitry needed to power IR sources 269, 271, 273 through electrical conduits 287, 289, 291 respectively, and to power, if necessary, and to receive detected IR light information from detectors 275, 277, 279 through electrical conduits 293, 295, 297 respectively. Electronics 7 is powered through electrical conduit 39 and communicates information with other apparatus (not shown) through electrical conduit 41.

Schematic cross sections through apparatus 251 along diameters 281, 283, 285 would appear similar to cross sections shown in FIGS. 2, 3. The relative placement of source 269, 271 or 273, the placement of the respective detector 275, 277 or 279, and the shape of the IRE 253 convex surface 257 determine the number of reflections that light from the sources makes before being received by the detectors. The rod-section shape of IRE 253 requires greater precision placing/aligning sources than is necessary with the hemisphere shape of IREs of previous embodiments. The symmetry of a hemispherical IRE is such that any source light emitted perpendicular to the line between the source and the detector is focused on the detector, whereas the symmetry of rod-section IRE 253 is such that the only light focused on detectors 275, 277, 279 from respective sources 269, 271, 273 is light that is not only perpendicular to diameters 281, 283, 285 respectively but also perpendicular to essentially flat surface 259 of the IRE. Nonetheless, with proper placement and alignment, a substantial portion of the light emitted by sources 269, 271, 273 is received at detectors 275, 277, 279 respectively after a designed number of reflections from surface 257 of IRE 253.

In operation, power is applied to electronics 7 of apparatus 251 through electrical conduit 39. Since detectors 275, 277, 279 each receive a unique frequency, sources 269, 271, 273 can be powered together when electronics 7 is powered, or when determined either by a controller in the electronics or by information communicated through electrical conduit 41 from an external controller (not shown). To minimize unwanted light at detectors 275, 277, 279 that is not from respective sources 269, 271, 273, or for other reasons, such as to limit the maximum power requirement of apparatus 251, the sources can be powered independently when determined by a controller in electronics 7 or by information communicated through electrical conduit 41 from an external controller. In any case, if no fluid is in contact with surface 257 of IRE 253, the amount of light received at each detector 275, 277, 279 from corresponding source 269, 271, 273 respectively, and light from other sources powered at the same time, is 100% reflectance of the detector frequency light. The amount of light received at each detector 275, 277, 279, under the same conditions, when fluid is in contact with surface 257 of IRE 253 is a function of the position of the detector and source or sources 269, 271, 273 for each light path and the fluid's single-surface-reflectance at the detector's frequency. With the position of detectors 275, 277, 279 and sources 269, 271, 273 fixed in base 255, relatively exact equations can be calculated or empirical curves can be fit that allow a fluid's single-surface-reflectance at the detector frequencies to be determined. In any case, electronics 7 of apparatus 251 communicates information relevant to the light received at detectors 275, 277, 279 through electrical conduit 41.

While FIG. 12 shows an embodiment with three light paths, another embodiment can have only two or greater than three light paths. Indeed, the length of a cylindrical-section shaped IRE, such as IRE 253 of FIG. 12, can be designed to accommodate a specific number of light paths needed to monitor the frequencies of interest for a fluid in a particular application.

Invention embodiments shown thus far have an IRE with only one essentially flat surface. An IRE of the present invention, however, can have multiple flat surfaces.

Figure 13:
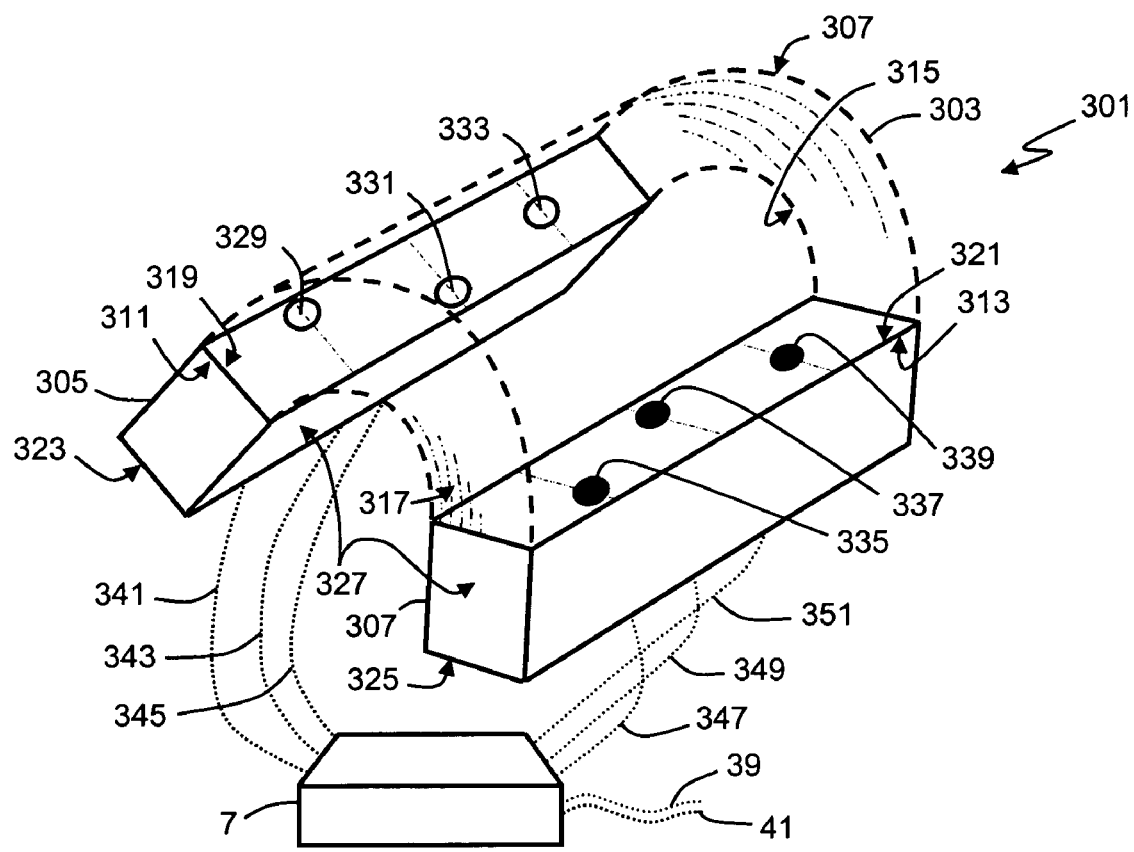
FIG. 13 is a schematic illustration showing an embodiment of the present invention with an essentially longitudinal-tube-section shaped IRE and with three IR light paths having independent sources and independent detectors.

FIG. 13 shows a schematic illustration of an on-line fluid monitoring apparatus of the present invention. Apparatus 301 includes IR transparent IRE 303, two mounting bases 305, 307 and electronics 7. IRE 303 is a solid of appropriate index-of-refraction with a shape that is essentially a section of a tube cut along the tube axis including convex surface 309, two essentially flat surfaces 311, 313, a concave surface 315 and two ends generally labeled 317. Bases 305, 307 include essentially-flat upper surfaces 319, 321 respectively, lower surfaces 323, 325 and side surfaces generally labeled 327. Surface 319 of base 305 is fixedly attached to surface 311 of IRE 303, and surface 321 of base 307 is fixedly attached to surface 313 of the IRE. Although not shown, side surfaces 327 of bases 305, 307 include attachment means or are incorporated in a package that has attachment means that allows apparatus 301 to be mounted in a fluid container in a substantially leak free manner with fluid contacting convex surface 309 of IRE 303, but not contacting lower surfaces 323, 325 of bases 305, 307 respectively and electronics 7. Base 305 includes three broadband IR light sources 329, 331, 333, and also lenses shown in FIGS. 14, 15, that are fixedly held in the base. Base 307 includes three IR detectors 335, 337, 339, and also filters shown in FIGS. 14, 15, that are fixedly held in the base. Detectors 335, 337, 339 are mounted across IRE 303 from sources 329, 331, 333 respectively in planes that are perpendicular to the axis of the IRE as shown by the phantom lines, and are positioned to allow light from a particular source to reflect a designed number of times from convex surface 309 of IRE 303 before being received by the detector that is in the same plane. Electronics 7 includes electronic circuitry needed to power IR sources 329, 331, 333 through electrical conduits 341, 343, 345 respectively, and to power, if necessary, and to receive detected IR light information from detectors 335, 337, 339 through conduits 347, 349, 351 respectively. Electronics 7 is powered through electrical conduit 39 and communicates information with other apparatus (not shown) through electrical conduit 41.

Figure 14:
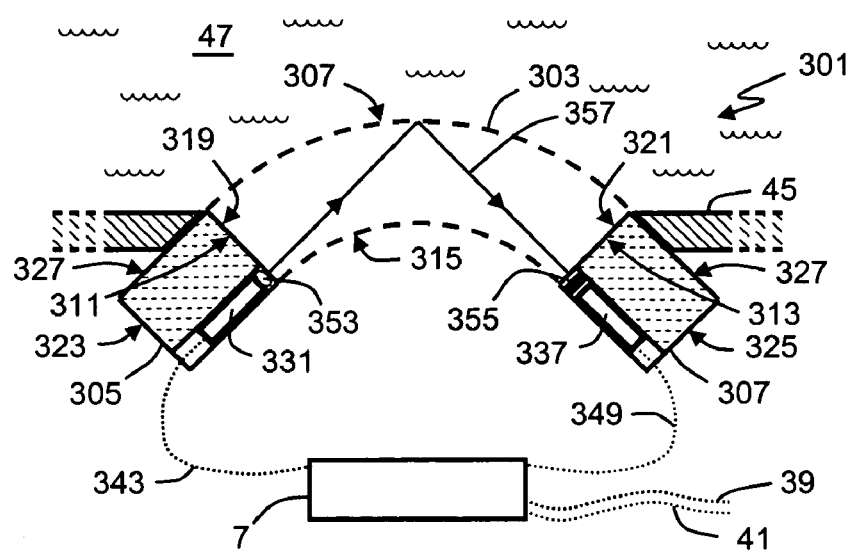
FIG. 14 is a schematic illustration of a cross section of the FIG. 13 apparatus showing a light path that has one reflection from the IRE convex surface.

FIG. 14 shows a schematic cross section of apparatus 301 of FIG. 13 taken through the plane that includes source 331 and detector 337. Apparatus 301 is mounted in fluid reservoir 45 with fluid 47 which surfaces 327 of bases 305, 307 mounted in a substantially leak free manner with reservoir 45 with convex surface 307 of IRE 303 in contact with fluid 47. As previously described source 331 is powered by electronics 7 through electrical conduit 343, and detector 337 communicates information to the electronics through electrical conduit 349. Lens 353 is fixedly held in base 305 between IR source 331 and flat surface 311 of IRE 303, and filter 355 is fixedly held in base 307 between detector 337 and flat surface 313 of IRE 303. Lens 353 aligns IR light emitted by source 331 so that in conjunction with the position of the source and the lens in base 305 and the shape of convex surface 307 of IRE 303, a substantial portion of the light emitted by the source is focused in a relatively small area along the same plane as the source after making one reflection with the convex surface as shown by light ray 357. Filter 355 and detector 337 are positioned so that the once-reflected light of ray 357 from source 331 is filter to determined frequencies before being received by the detector.

Figure 15:
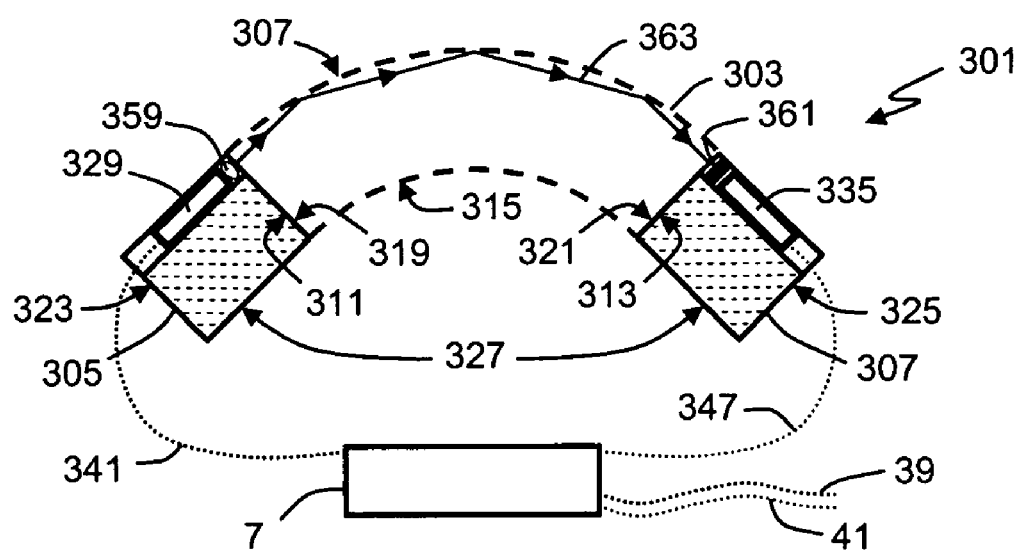
FIG. 15 is a schematic illustration of a cross section of the FIG. 13 apparatus showing a light path that has three reflections from the IRE convex surface.

FIG. 15 shows a schematic cross section of apparatus 301 of FIG. 13 taken through the plane that included source 329 and detector 335. As previously described source 229 is powered by electronics 7 through electrical conduit 341, and detector 335 communicates information to the electronics through electrical conduit 347. Lens 359 is fixedly held in base 307 between IR source 329 and flat surface 311 of IRE 303, and filter 361 is fixedly held in base 307 between detector 335 and flat surface 313 of the IRE. Lens 359 aligns IR light emitted by source 329 so that in conjunction with the position of the source and the lens in base 305 and the shape of the convex surface 307 or IRE 303, a substantial portion of the light emitted by the source is focused in a relatively small area along the same plane as the source after making three reflections with the surface as shown by light ray 363. Filter 361 and detector 335 are positioned so that thrice-reflected light of ray 363 from source 329 is filtered to determined frequencies before being received by the detector.

In operation, power is applied to electronics 7 of apparatus 301 through electrical conduit 39. Since filters 355, 361 and a similar filter (not shown but for descriptive convenience named 363) in front of detector 339 allow detectors 337, 335, 339 respectively to receive only a unique frequency, sources 329, 331, 333 can be powered together when electronics 7 is powered, or when determined either by a controller in the electronics or by information communicated through electrical conduit 41 from an external controller (not shown). To minimize unwanted light at detectors 335, 337, 339 that is not from respective sources 329, 331, 333, or for other reasons, for example to limit the maximum power needed to operate apparatus 301, the sources can be powered independently when determined by a controller in electronics 7 or by information communicated through electrical conduit 41 for an external controller. If no fluid is in contact with surface 307 of IRE 303, the amount of light received at each detector 335, 337, 339 from corresponding source 329, 331, 333 respectively, and light from other sources powered at the same time, is 100% reflectance of the filter 355, 361, 363 frequencies. The amount of light received at each detector 335, 337, 339, under the same conditions, when fluid is in contact with surface 307 of IRE 303 is a function of the position of the detector, and source or sources 329, 331, 333 for each light path and the fluid's single-surface-reflectance at the filter frequency of the light path. Electronics 7 of apparatus 301 communicates information relevant to the light received at detectors 335, 337, 339 through electrical conduit 41.

While FIG. 13 shows an embodiment of the invention with three light paths, other embodiments can have only two or greater than three light paths.

While FIG. 13 shows an embodiment of the invention with an IRE with less than a 180° section of a tube, another embodiment can have an IRE that is a section of a tube that is greater than 180° (but obviously less than 360°). As shown in FIG. 14, the IRE 303 with an approximately 90° section allows for a light path of only one light reflection with source 331 and detector 337 positioned normal to the essentially flat surfaces 311, 313 respectively of the IRE. A section greater than 180° allows easier design and construction of on-line fluid monitoring apparatus with a higher number of reflections.

While the invention of FIG. 13 is shown and described in FIG. 14 to have fluid in contact with convex surface 307 of IRE 303 and not in contact with concave surface 315 of the IRE, an invention embodiment can have bases 305, 307 mounted such that both surfaces 307, 315 are in contact with the fluid as long as the sensors 329, 331, 333, detectors 335, 337, 339, electronics 7 and other components are appropriately protected from the fluid.

While the invention of FIG. 13 is shown with two bases 305, 307, another embodiment can have a single base with essentially flat surfaces at the angles and locations of surfaces 319, 321.

The embodiments shown and described thus far have an IRE with the entire convex surface capable of being in contact with a fluid to be monitored by the invention. The IRE of the present invention, however, can have portions of the convex surface that can not contact a fluid.

Figure 16:
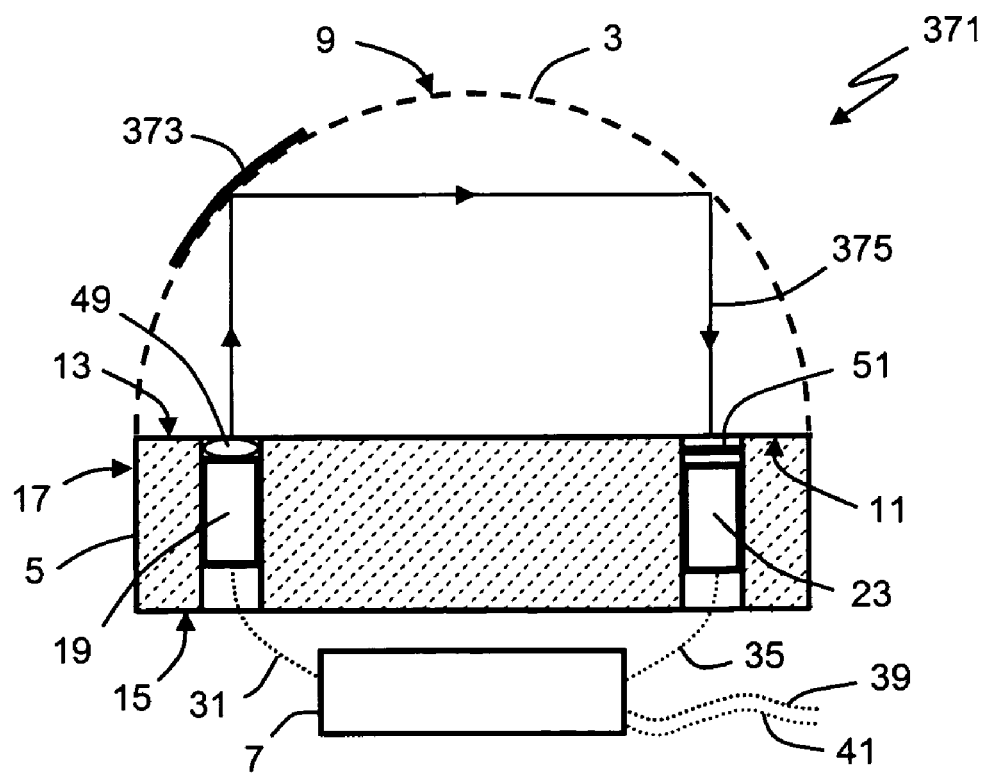
FIG. 16 is a schematic illustration of a cross section of an invention embodiment with a reflective covering preventing fluid contact with a portion of an IRE convex surface.

FIG. 16 shows a schematic illustration that is a cross section of an on-line fluid monitoring apparatus in accordance with aspects of the present invention. Apparatus 371 is similar to apparatus 1 of FIG. 2 and for convenience similar features are labeled the same. Apparatus 371 includes IR transparent IRE 3, mounting base 5 and electronics 7. IRE 3 is a solid of appropriate index-of-refraction with a hemispherical shape, as shown in FIG. 1, that includes convex surface 9 and flat surface 11. IRE 3 includes reflective coating 373 that covers a portion of convex surface 9 to prevent fluid from being able to contact the surface under the coating, and to reflect essentially 100% of any IR light internal to the IRE striking the convex surface under the coating. Base 5 is cylindrical in shape with upper-surface 13 fixedly attached to surface 11 of IRE 3, side-surface 17 including attachment means (not shown) to allow apparatus 371 to be mounted in a fluid container (not shown) in a substantially leak free manner with those portions of surface 9 of IRE 3 not covered with coating 373 to contact a fluid, but to prevent fluid from contacting base lower-surface 15 and electronics 7. Base 5 also includes IR source 19, lens 49, IR detector 23 and unique frequency filter 51 positioned such that a substantial light emitted by the source is twice reflected, as shown by light ray 375, from convex surface 9 of IRE 3 before light of the filter frequency is received by the detector. Electronics 7 powers source 21 through electrical conduit 31 and powers, if necessary, and receives detected IR light information from detector 23 through electrical conduit 35. Electronics 7 is powered through electrical conduit 39 and communicates information with other devices (not shown) through electrical conduit 41.

In operation, when electronics 7 of apparatus 371 applies power to IR source 19, as in apparatus 1 of FIG. 2, when no fluid is in contact with any portion of surface 9 of IRE 3, the amount of light received at detector 23 is essentially 100% reflectance of the filter 51 frequency light from source 19. When apparatus 371 is in a fluid with power applied to IR source 19, since at the one reflection point of the light path coating 373 prevents the fluid from contacting surface 9 of IRE 3 and, as with no fluid, reflects 100% of the light, the amount of light received at detector 23 is approximately the 100% reflectance amount times the fluid's percent reflectance at filter 51 frequency for one reflection divided by 100. Hence, with coating 373, hemispherical IRE 3 with single flat surface 11 can have a light path that has primarily only one reflection where convex surface 9 can contact a fluid.

While FIG. 16 is shown and described with a coating affecting the designed number of reflections a single light path makes from a convex surface that can contact a fluid, another embodiment can have a single coating placed that affects the designed number of reflections multiple light paths make from at least one convex surface that can contact a fluid.

While FIG. 16 has a coating covering only one portion of a single convex surface to prevent fluid from contacting the IRE surface, other embodiments can have coatings covering one or more portions of one or more convex IRE surfaces as part of the design to determine the number of reflections of one or more light paths make from at least one convex surface that can contact a fluid.

While FIG. 16 is described with a coating with 100% reflectance at the desired frequency to prevent fluid from contacting a convex surface 9 of IRE 3, another embodiment can have an IRE convex surface covered by a coating, of any thickness, to preventing fluid from contacting the surface where a light path is reflected, and the material reflectance at the light path frequency can be less than 100%, but must be greater than 0%; with a material with light reflectance greater than 75% preferred, a material with light reflectance greater than 90% more preferred, and a material with light reflectance greater than 95% most preferred.

The embodiments shown and described thus far have an IRE with one convex surface. Other embodiments of the invention include IRE can have essentially multiple convex surfaces.

Figure 17:
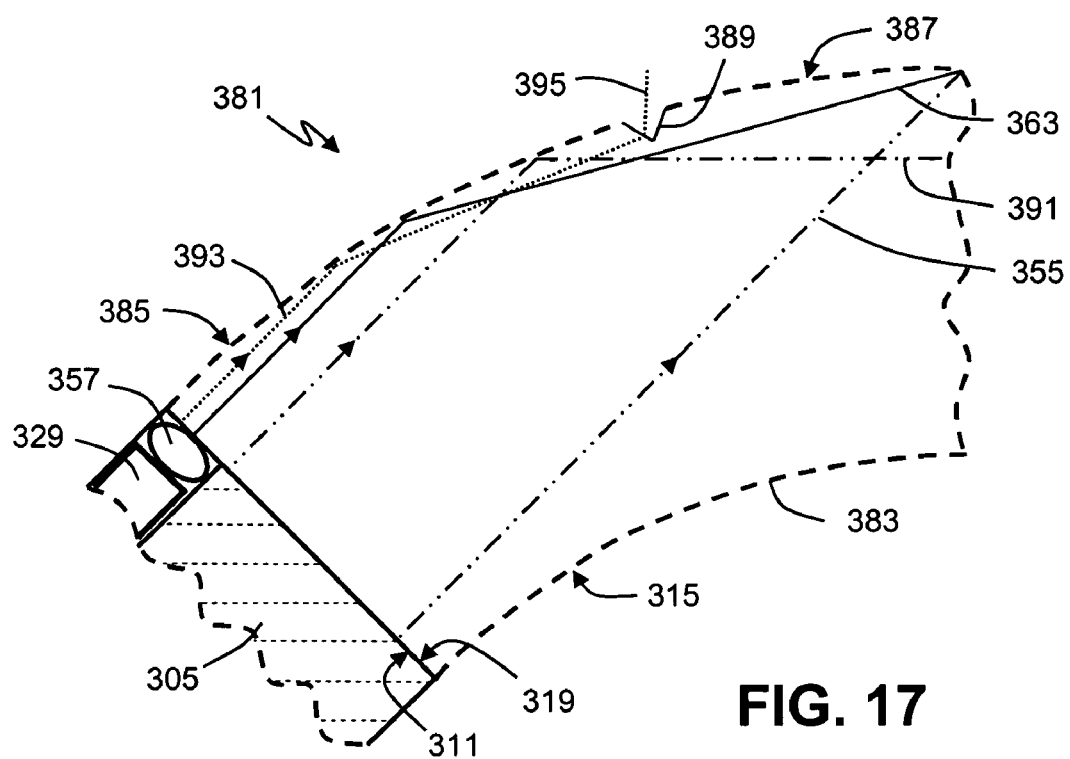
FIG. 17 is a schematic illustration of a cross section of an invention embodiment with two convex IRE surfaces separated by a groove that limits the number of reflections light can make within the IRE.

FIG. 17 shows a schematic illustration that is a partial cross section of an on-line fluid monitoring apparatus of the present invention. Apparatus 381 is similar to apparatus 301 shown in cross section in FIG. 15, and for convenience similar features are labeled the same. Apparatus 381 includes IR transparent IRE 383 and mounting base 305. IRE 383 is a solid of appropriate index-of-refraction with a shape similar to IRE 303 of FIGS. 13, 14, 15; that is, essentially a section of a tube cut along the tube axis that includes concave surface 315 and flat surface 311. However, unlike IRE 303 which has a single convex surface 307, IRE 383 has two concave surfaces 385, 387 that are separated by a groove 389 that is parallel to the axis and along the full length of the IRE. Base 305 includes essentially-flat upper-surface 319, which is fixedly attached to surface 311 of IRE 383, and IR source 329 and lens 357 that are fixedly attached to the base. Source 329 and lens 357 are positioned to allow a substantial portion of the emitted light to be received by a detector (not shown) after three reflections, one from convex surface 385 and two from convex surface 387 (one reflection not shown) with IRE 383 as indicated by light ray 363. Also shown are phantom lines for: light ray 355, which makes one reflection with surface 387 of IRE 383 if an IR source were located in the position shown for source 331 in FIG. 14; light ray 391, which makes two reflections with the surfaces of the IRE if a source were at a location in a position at the end of the light path; and, light ray 393, which would make four reflections with the surfaces of the IRE if groove 389 were not in the IRE. With groove 389 present, the light of ray 393 strikes a side surface of the groove, that, because of the groove angle, causes the light of ray 393 to be transmitted out of IRE 383 (shown as ray 395 outside of the IRE) instead of being reflected internally.

In operation, when source 329 of apparatus 381 is powered, lens 357 aligns a substantial portion of the IR light emitted by the source to make three reflections of ray 363 in IRE 383 before being received at a unique frequency by a detector (not shown). However, due to the size of source 329 and lens 357 relative to the size of IRE 383, a portion of the light from the source is emitted along ray 393, which, if groove 389 were not present, would be received by the detector after 4 reflections. Also due to the size of source 329 and lens 357, a portion of the emitted light may be reflected greater than four times if groove 389 were not present. As previously described, relatively exact equations can be calculated or empirical curves can be fit that allow a fluid's single-surface-reflectance to be determined where a light path between a source and detector includes a number of reflections greater, or less, than the primary number of reflections, for example the three reflections of ray 363. An issue with the path including light that makes a greater than the primary number of reflections is that while the portion of light the makes a greater number of reflections adds to the 100% reflectance of the light path, that is the reflectance when no fluid is in contact with the convex surface of an IRE, for example, surface 307 of IRE 303 in FIG. 15, when fluid is in contact with the convex surface light absorption for the portion with greater number of reflections is greater than for the light absorption for the light that makes the primary number of reflections. This results in the light path being more sensitive to fluid change near 100% reflectance than at lower reflectance percentages for the path's unique frequency. In some applications, this greater sensitivity near 100% reflectance may be desired and can actually be designed into the apparatus. In the application of apparatus 381, however, greater sensitivity near 100% reflectance is undesired and groove 389 separating convex surfaces 385, 387 separated effectively limits a portion of the light that makes from source 329 that would otherwise make greater than three reflections in IRE 383 before being received at the light path's detector. Groove 389 is positioned to not affect light paths shown by rays 355, 391, 363, which make one, two and three reflections respectively in IRE 383.

FIG. 17 shows an embodiment with a groove separating two IRE convex surfaces that transmits light in paths near the surfaces out of the IRE, other embodiments can have other discontinuities at or near the IRE surface that effectively separate two or more convex surfaces by one of the following: transmitting unwanted light out of the IRE; reflecting unwanted light in a direction that is not received by a detector; absorbing unwanted light.

Figure 18:
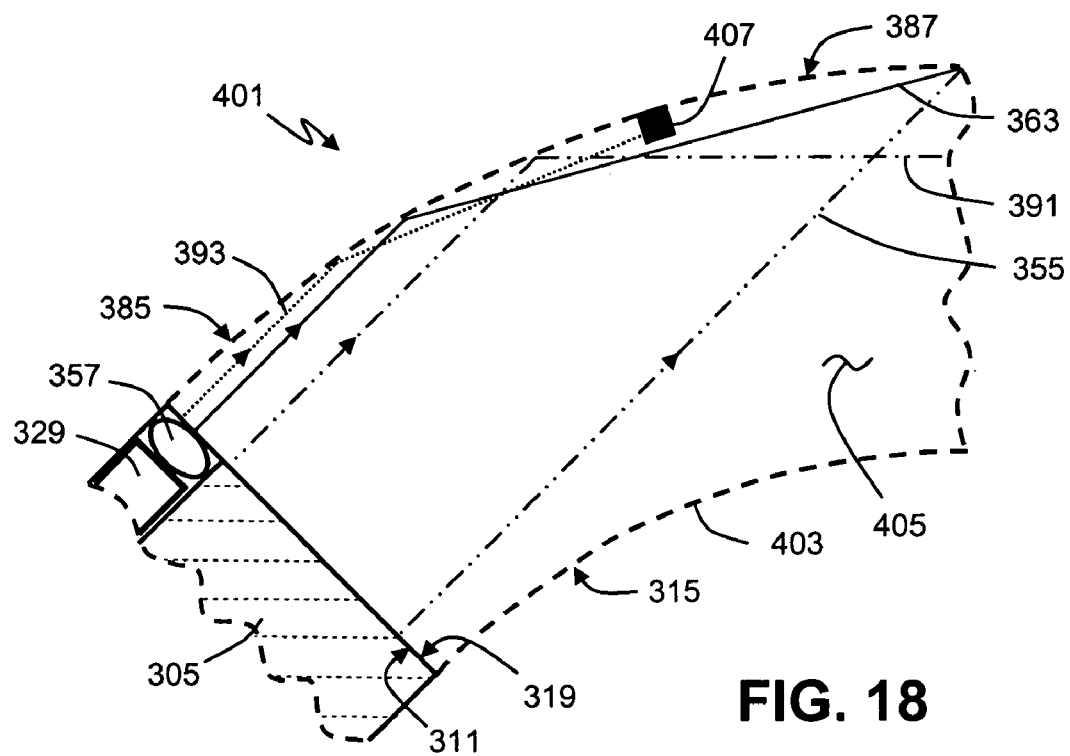
FIG. 18 is a schematic illustration of a cross section of an embodiment of the present invention with essentially two convex IRE surfaces separated by an IRE section of different chemical composition that limits the number of reflections light can make within the IRE.

FIG. 18 shows a schematic illustration that is a partial cross section of an on-line fluid monitoring apparatus in accordance with aspects of the present invention. Apparatus 401 is similar to apparatus 381 of FIG. 17, and similar features are labeled the same. Apparatus 401 includes IRE 403 and mounting base 305. IRE 403 is a solid with shape similar to IRE 383 of FIG. 17. However, unlike IRE 383, and all of the previously shown IREs, IRE 403 is comprised of two materials, material 405 that is IR transparent and has index-of-refraction appropriate for the unique IR frequencies of interest for apparatus 401, and material 407 that absorbs IR light at the unique IR frequencies of interest. Material 407, which is significantly chemically different than material 405, is placed either in conjunction with or after the manufacture of material 405. IRE 403 has concave surface 315, flat surface 311 and two concave surfaces 385, 387 that are effectively separated by material 405 that is parallel to the axis and along the full length of the IRE. Base 305 includes essentially-flat upper-surface 319, which is fixedly attached to surface 311 of IRE 403, and IR source 329 and lens 357 that are fixedly attached to the base. As in the embodiment of FIG. 17, source 329 and lens 357 are positioned to allow a substantial portion of the emitted light to be received by a detector (not shown) after three reflections, one from convex surface 385 and two from convex surface 389 (one reflection not shown) with IRE 403 as indicated by light ray 363. Also shown are phantom lines for: light ray 355 which makes one reflection with surface 387 of IRE 403 if an IR source were located in the position shown for source 331 in FIG. 14; light ray 391, which makes two reflections with the surfaces of the IRE if a source were at a location in a position at the end of the light path; and, light ray 393, which would make four reflections with the surfaces of the IRE if material 405 were not included in the IRE. With material 405 present, the light of ray 393 is absorbed and the ray terminated by the material.

In operation, when source 329 of apparatus 401 is powered a substantial portion of the emitted IR light make the three reflections of ray 363 before being received at a unique frequency by a detector (not shown). However, due to the size of source 329 and lens 357 relative to the size of IRE 403, a portion of the light from the source is emitted along ray 393, which, if material 407 were not present, would be received by the detector after 4 reflections. Also due to the size of source 329 and lens 357, a portion of the emitted light may be reflected greater than four times if material 407 were not present. As described for apparatus 381 of FIG. 17, eliminating paths with higher numbers of reflections than the primary path can reduce unwanted greater sensitivity of apparatus 401 to fluid single-surface-reflectance near 100% at the light path frequency. That is, material 407 separating convex surfaces effectively limits some of the paths with greater than three reflections in IRE 403. Material 407 is appropriately sized and positioned to not affect light of rays 355, 391, 363 making one, two and three reflections respectively in IRE 403.

While material 407 shown in FIG. 18 is described as a material that absorbs IR light of the unique light path frequency to essentially separate the two convex surfaces, another embodiment can have material of appropriate index-of-refraction and shape that transmits the light from the unwanted paths out of the IRE or that reflects light from the unwanted paths in a direction that is not received by a detector.

While material 407 shown in FIG. 18 is described as a material that is substantially chemically different than material 405, another embodiment can have chemically similar materials 405, 407 that differ only in the concentration of certain elements. For example, an IRE can be a semiconductor that when doped to one level is IR transparent at the required frequencies, and when doped to a different level or by a different element is an IR light absorber.

While material 407 shown in FIG. 18 is described as absorbing all light at the desired frequency, another embodiment can have a material that absorbs light at less than 100% absorbance; however, a material with light absorbance greater than 75% is preferred, a material with light absorbance greater than 90% is more preferred, and a material with light absorbance greater than 95% is most preferred.

While FIG. 18 shows a material internal to the IRE that absorbs light from unwanted paths, another embodiment can have a material external to the IRE that absorbs the light and essentially separates convex surfaces of the IRE.

Figure 19:
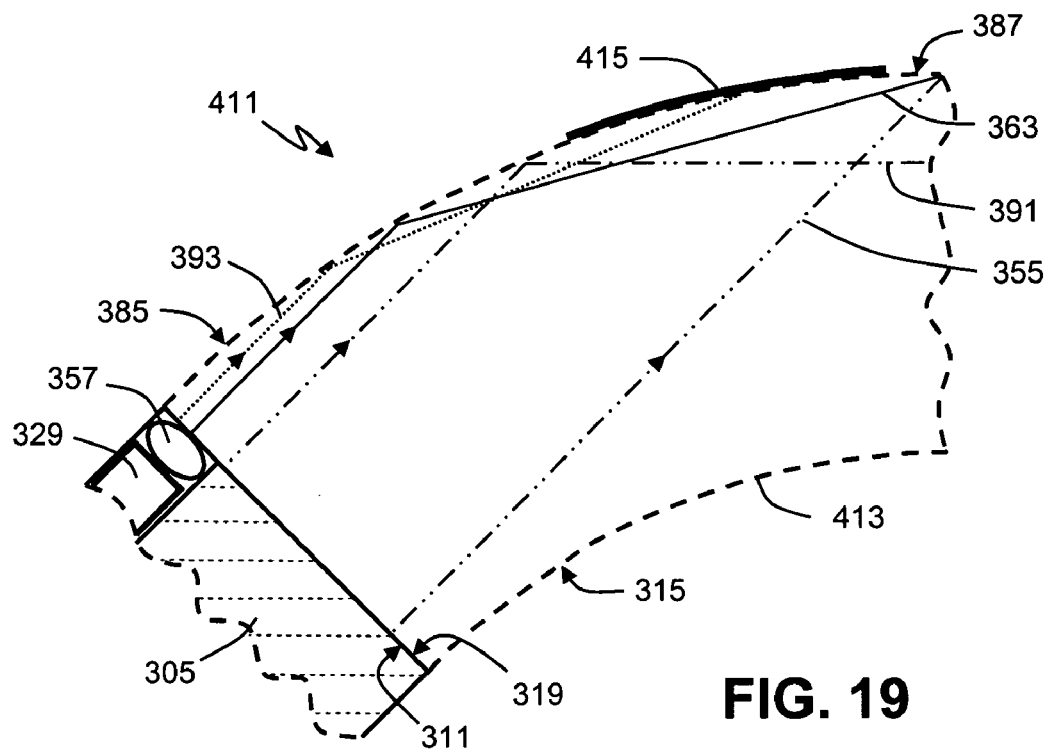
FIG. 19 is a schematic illustration of a cross section of an embodiment of the present invention with essentially two convex IRE surfaces separated by surface covering that absorbs IR light to limit the number of reflections light can make within the IRE.

FIG. 19 shows a schematic illustration that is a partial cross section of an on-line fluid monitoring apparatus in accordance with aspects of the present invention. Apparatus 411 is similar to apparatus 381 of FIG. 17 and similar features are labeled the same. Apparatus 411 includes IR transparent IRE 413 and mounting base 305. IRE 413 is a solid of appropriate index-of-refraction with the same shape as IRE 303 of FIGS. 13, 14, 15. IRE 413 has two concave surfaces 385, 387 that are essentially separated by an IR light absorbing coating 415 that is parallel to the axis and along the full length of the IRE. Base 305 includes the same features as base 305 in FIGS. 17, 18, is fixedly attached to IRE 413, and has source 329 and lens 357 positioned to allow a substantial portion of the emitted light to be received by a detector (not shown) after three reflections as indicated by light ray 363 (one reflection not shown). Also shown are phantom lines for: light ray 355, which makes one reflection with surface 387 or IRE 413 if an IR source were located in the position shown for source 331 in FIG. 14; light ray 391, which makes two reflections with the surfaces of the IRE if a source were at a location in a position at the end of the light path; and, light ray 393, which would make four reflection with the surfaces of the IRE if coating 415 were not on the surface of the IRE.

In operation, when source 329 of apparatus 411 is powered, lens 357 aligns a substantial portion of the IR light emitted by the source to make three reflections of light ray 363 in IRE 413 before being received at a unique frequency by a detector (not shown). However, due to the size of the source 329 and lens 357 relative to the size of IRE 413, a portion of the light from the source is emitted along light ray 393, which, if coating 415 were not present would be received by the detector after 4 reflections. Also due to the size of source 329 and lens 357, a portion of the emitted light may be reflected greater than four times if coating 415 were not present. As described for apparatus 381 of FIG. 17, eliminating paths with higher numbers of reflections that the primary path can reduce unwanted greater sensitivity of apparatus 411 to fluid single-surface-reflectance near 100% of the light path frequency. That is, coating 415, by absorbing all IR light that contacts the IRE 413 surface under the coating, effectively limits some of the paths with greater than three reflections in the IRE. Coating 415 is appropriately sized and positioned to not affect rays 355, 391, 363, which make one, two and three reflections respectively in IRE 413.

While coating 415 of FIG. 19 is described as absorbing 100% of the IR light that contacts the IRE 413 surface under the coating, other embodiments can have a coating that has less than 100% absorbance; however, a material with light absorbance greater than 75% is preferred, a material with light absorbance greater than 90% is more preferred, and a material with light absorbance greater than 95% is most preferred.

FIGS. 17, 18, and 19 show two convex surfaces that are separated essentially perpendicularly to a light path. The present invention, however, is not limited to only two convex surfaces or to surfaces separated essentially perpendicular to a light path.

Figure 20:
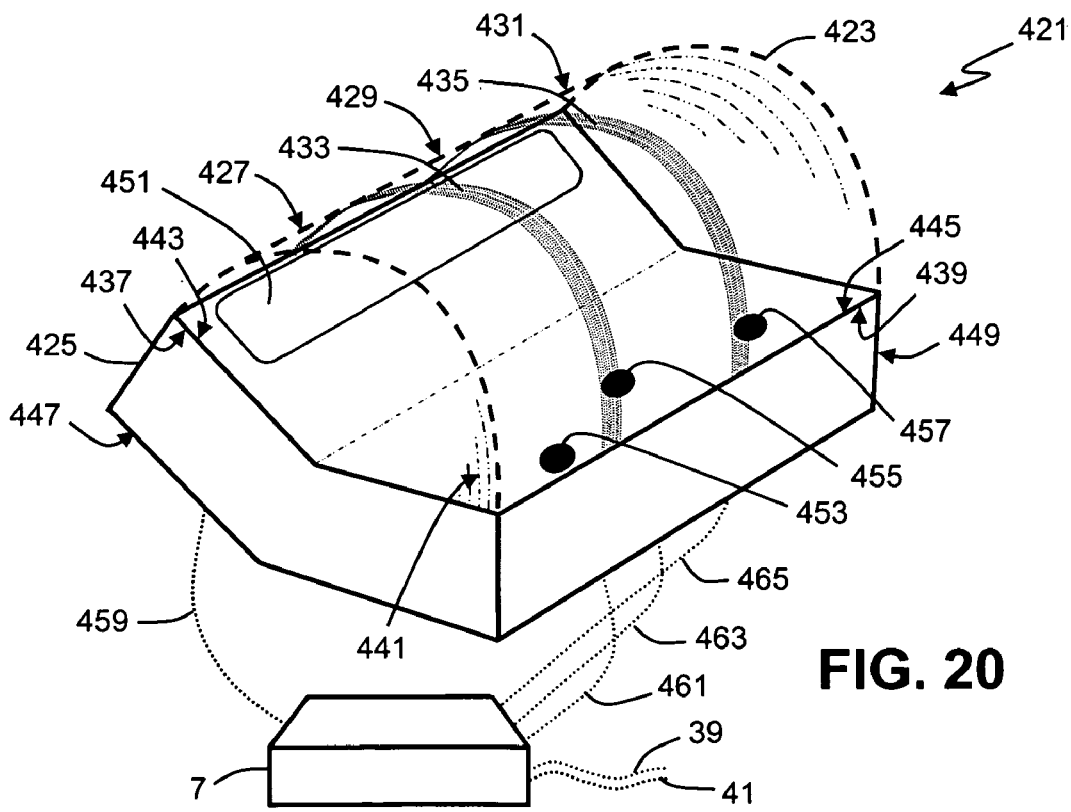
FIG. 20 is a schematic illustration showing an embodiment of the present invention with an IRE having three convex surfaces and with three IR light paths having independent detectors and common source.

FIG. 20 shows a schematic illustration of an on-line fluid monitoring apparatus in accordance with aspects of the present invention. Apparatus 421 includes IR transparent IRE 423, mounting base 425 and electronics 7. IRE 423 is a solid of appropriate index-of-refraction with a shape that is essentially a less than 180° section of a cylinder cut along the cylinder axis and that includes convex surfaces 427, 429, 431 that are separated by bands 443, 445 of roughened surface (for example, grit blasted surface), essentially-flat surfaces 447, 449 and two ends, generally labeled 451. Base 423 has essentially-flat upper surfaces 443, 445, lower surfaces generally labeled 447 and side surfaces generally labeled 449. Surfaces 453, 455 of base 425 are fixedly attached to surfaces 437, 439 respectively of IRE 423. Although not shown, side surfaces 459 of base 423 include attachment means or are incorporated in a package that has attachment means that allows apparatus 421 to be mounted in a fluid container in a substantially leak free manner with fluid contacting convex surfaces 427, 429, 431 of IRE 423 but not contacting lower surface 447 of base 425 and electronics 7. Base 425 includes one broadband IR light source 451 fixedly held and positioned to emit light from base upper surface 443 into flat surface 437 or IRE 423, and three unique frequencies IR light detectors 453, 455, 457, each fixedly held and positioned of receiving light at base surface 445 from IRE surface 439 after a designed number of reflections from the IRE convex surfaces 427, 429, 431. In particular, detector 453 is positioned to primarily receive a unique light frequency from source 451 after three reflections from convex surface 427 of IRE 423, detector 455 is positioned to primarily receive another unique light frequency from source after one reflection from IRE convex surface 429, and detector 457 is positioned to primarily receive a third unique light frequency from the source after two reflections from IRE convex surface 431. Electronics 7 includes electronic circuitry to power IR light source 451 through electrical conduit 459, and to power, if necessary, and to receive detected IR light information from detectors 453, 455, 457 through electrical conduits 461, 463, 465 respectively. Electronics 7 is powered through electrical conduit 39 and communicates information with other apparatus (not shown) through electrical conduit 41.

In operation, power is applied to electronics 7 of apparatus 421 through electrical conduit 39. Since there is only one source 451, power can be applied to the source when electronics 7 is powered, or when determined either be a controller in the electronics or by information communicated through electrical conduit 41 from an external controller (not shown). As described above, detectors 453, 455, 457 are positioned to receive unique frequencies of the light emitted by source 451 after a primary number of reflections form convex surfaces 427, 429, 431 respectively of IRE 423. However, due to the relatively large size of source 441, detectors 453, 455, 457 may receive light that makes a greater number, or in the cases of detectors 453, 457 a lesser number, of reflections with the respective convex surfaces 427, 429, 431. Also the detectors 453, 455, 457 may receive light that makes a greater number, or again in the cases of detectors 453, 457 a lesser number, of reflections with some of the reflections coming from other than their respective convex surfaces 427, 429, 431 if not for roughened surfaces 433, 435. Roughened surfaces 433, 435 are of appropriate size and are properly positioned to minimize the reflection of light from source 451 to detectors 453, 455, 457 that has other than the designed primary number of reflections. In any case, if no fluid is in contact with surfaces 427, 429, 431 of IRE 423, the amount of light received at each detector 453, 455, 457 from source 451 is 100% reflectance of the detector frequency light. The amount of light received at each detector 453, 455, 457 when fluid is in contact with surfaces 427, 429, 431 is a function of the fluid's single-surface-reflectance at the detector's frequency. Electronics 7 of apparatus 421 communicates information relevant to the light received at detectors 453, 455, 457 through electrical conduit 41.

While FIG. 20 shows roughened surfaces that are circumferential to the cylindrical-shaped IRE to minimize the sensors reception of light from the source that has other than the designed primary number of reflections, another embodiment can have tangential roughened surfaces (or grooves or chemically different materials as shown in FIGS. 17, 18 respectively) in addition to the circumferential grooves to minimize reception of light that does not have the designed primary number of reflections.

While FIG. 20 shows electronics 7 to be independent of base 425, in another embodiment, apparatus 421 may be packaged to have the base with IRE 423 and the electronics within a single unit. Actual packaging is not critical other than in terms of the operation and function described, and is dependent on cost, performance and size constraints of the particular application for which the apparatus is designed.

While particular embodiments of the present invention have been shown and described, various combinations, changes and modification may be made therein to meet fluid analysis needs of various applications without departing from the invention in its broadest aspects. In particular, with regard to various functions performed by the above described invention, the terms (including any reference to a "means") used to describe individual components or subsystems of the invention are intended to correspond, unless otherwise indicated, to any component or sub-system which performs the specified function of the described component or sub-system (e.g. that is functionally equivalent), even though not structurally or electronically equivalent to the described component or sub-system which performs the function in the herein illustrated embodiments of the invention. In addition, while a particular feature of the invention may have been disclosed with respect to only one of several embodiments, such feature may be combined with one or more other features of the other embodiments as may be desired and advantageous for any given or particular application.

What is claimed is:
1. An apparatus comprising:
a) an IR transparent internal reflectance element (IRE) with at least one essentially flat surface and at least one convex surface that can contact a fluid,
b) at least two IR light paths of different frequencies with emitted light from one or more source entering a flat surface of the IRE, internally reflecting at least once from a convex surface of the IRE that can contact a fluid, exiting a flat surface of the IRE, and being received at one or more detectors; wherein a determined frequency of the different frequencies of a said light path is determined by at least one of the following: a) the light path's source only emits light at the determined frequency, b) each of the light path's detector only receives light at the determined frequency, e) and an optical filter of the determined frequency is placed between the light path's source and the detector, and c) combinations thereof, and
c) electronics to power the light paths, independently monitor the amount of light received for each light path, and communicate information relevant to the monitored light reception wherein the number of reflections that a said light path makes from at least one convex surface of the IRE, which can contact the fluid, is determined by at least one of the following a) a shape of the IRE, b) a surface property of the IRE, c) a relative position at a said IRE flat surface that the light path's IR source light enters the IRE, d) a relative position at a said IRE flat surface that the light path's detector receives light that exits the IRE, and e) combinations thereof.

2. The apparatus of claim 1 wherein the source of a said light path includes at least one IR light emitter and wherein the detector of the light path includes at least one IR light sensor.

3. The apparatus of claim 1 wherein the amount of light received for a said light path is independently monitored using a controllable IR source that provides essentially all the light path's IR light wherein at least one of the following occurs: a) the source only emits light at the determined frequency, b) an optical filter of the determined frequency is placed between the source and the IRE, and c) combinations thereof.

4. The apparatus of claim 1 wherein the amount of light received for a said light path is independently monitored using a controllable IR detector that receives essentially all the light path's IR light wherein at least one of the following occurs; a) the detector only receives light of the determined frequency, b) an optical filter of the determined frequency is placed between the detector and the IRE, and c) combinations thereof.

5. The apparatus of claim 1 wherein the amount of light received for a said light path having a said source that emits a broadband IR light to multiple said light paths, and a said detector that receives a broadband IR light from multiple said light paths is independently monitored wherein at least one of the following occurs: a) between the source and the IRE, the path includes an optical filter of the determined frequency and an optical element that can be controlled to either allow light to pass or to be blocked in the path, b) between the detector and the IRE, the path includes an optical filter of the determined frequency and an optical element that can be controlled to either allow light to pass or to be blocked in the path, and c) combinations thereof.

6. The apparatus of claim 1 wherein the IRE shape is one of the following: a) essentially hemispherical, b) essentially a longitudinal rod section, c) essentially a longitudinal tube section, and d) combinations thereof.

7. The apparatus of claim 1 wherein the surface property of the IRE includes at least one of the following: a) a covering on a said convex IRE surface, b) a discontinuity that transmits light out of the IRE separating the convex surface sections, c) a discontinuity that reflects light in a direction that is not received by a said detector separating the convex surface sections, d) a discontinuity that absorbs substantially all IR light separating the convex surface sections, and e) combinations thereof.

8. The apparatus of claim 7 wherein the covering on the convex IRE surface reflects a determined quantity of IR light essentially independent of the fluid in contact with the covering.

9. The apparatus of claim 7 wherein a discontinuity separating the IRE convex surface sections includes at least one of the following: a) at least one groove in the surface; b) surface roughening, c) changes in material property of the IRE, and d) combinations thereof.

10. The apparatus of claim 1 wherein the relative position at the IRE flat surface that the light path's IR source light enters the IRE is determined by one of the following: a) a mounting location essentially adjacent to the IRE flat surface of the source's output, b) a mounting location essentially adjacent to the IRE flat surface of an output of an optical conduit communicating light from the source, and c) combinations thereof.

11. The apparatus of claim 1 wherein the relative position at the IRE flat surface that light path exits the IRE is determined by one of the following: a) a mounting location essentially adjacent to the IRE flat surface of the detector's input, b) a mounting location essentially adjacent to the IRE flat surface of the input of an optical conduit communicating light to the detector, and c) combinations thereof.

12. The apparatus of claim 1 wherein a said light path includes at least one of the following: a) a lens between a said source and the IRE to align light emitted from the source, b) a lens between the IRE and a said detector to limit the angle of light exiting the IRE that is received by the detector, and c) combinations thereof.

13. The apparatus of claim 1 wherein the electronics includes a control means to independently monitor the amount of light received for each of said light path.

14. The apparatus of claim 1 wherein the electronics uses an external control information to independently monitor the amount of light received for each of said light path.

15. The apparatus of claim 1 wherein the electronics communicate a detector electrical output of each of said light path as the information relevant to the monitored light reception.

16. The apparatus of claim 1 wherein the electronics include a means to convert a detector electrical output of each of said light path to suitable data and communicate those data as the information relevant to the monitored light reception.

17. The apparatus of claim 1 wherein the electronics include a means to analyze an IR detector electrical output of each of said light path to determine a property selected from the group comprising of a quality, a condition or a combination thereof of a fluid that contacts a said convex surface of the IRE and communicates that determination as the information relevant to the monitored light reception.

18. A process for on line monitoring of a fluid comprising:
  a) emitting light from at least one source to enter at least one essentially flat surface of an IRE,
  b) internally reflecting the light at least once from at least one convex surface of an IRE wherein the convex surface is in contact with a fluid and having the reflected light exit at least one essentially flat surface of the IRE, and wherein the number of reflections that a said light path makes from at least one convex surface of the IRE, which can contact the fluid, is determined by at least one of the following: a) a shape of the IRE, b) a surface property of the IRE, c) a relative position at a said IRE flat surface that the light path's IR source light enters the IRE, d) a relative position at a said IRE flat surface that the light path's detector receives light that exits the IRE, and e) combinations thereof,
  c) receiving at least a portion of the exiting light with at least one detector, and
  d) controlling light emitted from the at least one source and the reflected light received by the at least one detector such that at least two IR light paths of different frequencies are independently monitored, wherein the properties selected from the group comprising of a quality, a condition and combinations thereof of the fluid is being monitored; and wherein a determined frequency of the different frequencies of a said light path is determined by at least one of the following: a) the light path's source only emits light at the determined frequency, b) each of the light path's detector only receives light at the determined frequency, e) and an optical filter of the determined frequency is placed between the light path's source and the detector, and c) combinations thereof.

* * * * *